(12) United States Patent
Kapoor

(10) Patent No.: US 9,492,138 B2
(45) Date of Patent: Nov. 15, 2016

(54) MOBILE FRONT-END SYSTEM FOR COMPREHENSIVE CARDIAC DIAGNOSIS

(71) Applicant: Rijuven Corporation, Pittsburgh, PA (US)

(72) Inventor: Rajeshwar Kapoor, Pittsburgh, PA (US)

(73) Assignee: RIJUVEN CORP, Wexford, PA (US)

( * ) Notice: Subject to any disclaimer, the term of this patent is extended or adjusted under 35 U.S.C. 154(b) by 195 days.

(21) Appl. No.: 14/121,911

(22) Filed: Oct. 31, 2014

(65) Prior Publication Data

US 2015/0065814 A1  Mar. 5, 2015

Related U.S. Application Data

(63) Continuation-in-part of application No. 13/573,944, filed on Oct. 15, 2012, now abandoned.

(51) Int. Cl.
| | |
|---|---|
| *A61B 5/02* | (2006.01) |
| *A61B 7/04* | (2006.01) |
| *A61B 7/00* | (2006.01) |
| *A61B 5/0205* | (2006.01) |
| *A61B 5/0408* | (2006.01) |
| *A61B 5/00* | (2006.01) |
| *G06F 19/00* | (2011.01) |
| *A61B 5/113* | (2006.01) |
| *A61B 5/0472* | (2006.01) |

(52) U.S. Cl.
CPC ............... *A61B 7/04* (2013.01); *A61B 5/002* (2013.01); *A61B 5/02028* (2013.01); *A61B 5/02055* (2013.01); *A61B 5/04085* (2013.01); *A61B 5/6823* (2013.01); *A61B 7/00* (2013.01); *G06F 19/3418* (2013.01); *G06F 19/3431* (2013.01); *A61B 5/0472* (2013.01); *A61B 5/1135* (2013.01); *A61B 2560/0443* (2013.01)

(58) Field of Classification Search
CPC ........ A61B 7/04; A61B 5/02; A61B 5/0452; A61B 5/044; A61B 5/0006
USPC ............................ 600/513, 523, 528; 381/67
See application file for complete search history.

(56) References Cited

U.S. PATENT DOCUMENTS

| | | | | | |
|---|---|---|---|---|---|
| 4,071,694 | A  * | 1/1978 | Pfeiffer | ..................... | A61B 7/02 381/67 |
| 4,991,581 | A  * | 2/1991 | Andries | ................... | A61B 7/04 600/528 |
| 6,002,777 | A  * | 12/1999 | Grasfield | ................. | A61B 7/04 181/131 |
| 6,757,392 | B1 * | 6/2004 | Granzotto | ............ | A61B 5/0002 181/131 |
| 6,884,218 | B2 * | 4/2005 | Olson | ................ | A61B 5/04011 600/450 |
| 8,092,396 | B2 * | 1/2012 | Bagha | ....................... | A61B 7/04 381/67 |
| 2001/0030077 | A1* | 10/2001 | Watson | ................... | A61B 5/044 181/131 |
| 2002/0071570 | A1* | 6/2002 | Cohen | ...................... | A61B 7/04 381/67 |

(Continued)

*Primary Examiner* — Christopher D Koharski
*Assistant Examiner* — Jeremiah Kimball

(57) ABSTRACT

A stethoscope front-end recorder device (also referred to as Sleeve) for the chest piece of a stethoscope, which is easily installed and removed. The Sleeve is attached to the chest piece of a stethoscope for comprehensive diagnosis of heart issues. The Sleeve contains sensors for acquiring biosensor parameters such as electrocardiogram, body temperature, heartbeat, heart rhythm, heart rate variability, heart rate turbulence, heart sounds, respiration, cardiac index and blood flow. The Sleeve has Bluetooth interface communicating with a mobile device with software component, interfacing with a back-end server with the capability to capture, analyze and save patient information.

9 Claims, 20 Drawing Sheets

(56) References Cited

U.S. PATENT DOCUMENTS

| | | | |
|---|---|---|---|
| 2002/0111777 A1* | 8/2002 | David | A61B 5/4041 702/189 |
| 2003/0002685 A1* | 1/2003 | Werblud | A61B 7/04 381/67 |
| 2004/0076303 A1* | 4/2004 | Vyshedskly | A61B 7/04 381/67 |
| 2004/0220487 A1* | 11/2004 | Vyshedskiy | A61B 5/0002 600/513 |
| 2006/0025696 A1* | 2/2006 | Kurzweil | A61B 5/04525 600/509 |
| 2009/0316925 A1* | 12/2009 | Eisenfeld | A61B 7/008 381/67 |
| 2010/0274099 A1* | 10/2010 | Telfort | A61B 5/6843 600/300 |

* cited by examiner

MOBILE FRONT-END SYSTEM FOR COMPREHENSIVE CARDIAC DIAGNOSIS

REFERENCE TO CO-PENDING APPLICATION(S)

The present application is a continuation in part of U.S. Provisional Patent Application Ser. No. 13/573,944 filed on Oct. 15, 2012, which has a provisional 61/627,768, filed on Oct. 17, 2011, the entire disclosures of which are hereby incorporated by reference.

TECHNICAL FIELD

The present invention relates to medical devices, and more particularly, to a sleeve for the chest piece of a stethoscope, which is easily installed and removed for comprehensive cardiac diagnosis.

BACKGROUND OF THE PRIOR ART

The heart and body produce hundreds of specific sounds, including heart, lung, bowel, circulatory and Korotkoff sounds. These sounds and combinations thereof are indicative of normal and abnormal conditions. Knowledge of these sounds provides valuable diagnostic information to the physician. The art of listening to these sounds and using them as diagnostic aids is known as auscultation. Early human beings have been able to listen to these sounds by placing the ear to the chest or back of the patient. Later, the air column stethoscope was developed. The stethoscope has proven to be a valuable instrument for medical professionals. The standard air column stethoscope used by the medical profession employs a listening cup placed on the chest or back of the patient with the sound amplified by a simple bell and diaphragm into a standing air column terminating in earpieces for the physician's ears.

The conventional stethoscope has remained relatively unchanged since the last century. Many problems exist with the use of conventional stethoscopes. In general, conventional stethoscopes offer very subjective information. For example, the hearing capability of the user has direct impact on the sounds observed. When a loud sound is followed by a soft sound, difficulty exists in detecting and assessing the intensity of the soft sound. It is difficult to time an abnormal heart sound with respect to the phase of the heartbeat, an important aspect of murmur diagnosis. A fast beating heart can make both the recognition and timing of abnormal sounds difficult. This problem is often found with children and animals where heart rates are often much higher than in adult humans. External noise may often mask heart, lung, circulatory and Korotkoff sounds detected under non-ideal listening conditions. These and many other problems plague the conventional stethoscope.

In response, the field has developed electronic stethoscopes that detect and display as waveforms both audio (heart sound) and ECG (heart electrical activity), as well as presenting the heart sounds aurally. Little et al. (U.S. Pat. No. 4,362,164) describe a stethoscope having a detector head that includes a microphone and is selectably connectable to either a conventional chest-bell or an electrode chest-bell. The electrode chest-bell is adapted to pick-up electric heart signals, and the microphone to pick up body sounds. The electrode and microphone signals are sent to a separate monitoring unit to display both ECG and phonocardiographic waveforms. The conventionally detected body sounds are transmitted via air column tube directly to the user's ears. However, the Little device, and others like it, require connectivity (either via interconnect cable of wireless transmission) between the stethoscope and a separate display unit, and they are not easily transported about a physician's or other care staffs person. Again, although these devices also may be useful for their intended purpose, they too have their limitations.

Most efforts at visual display of heart data have been directed to the electrocardiographic wave pattern. Because the electrocardiographic wave pattern, i.e., the electrical wave pattern generated by the heart, is more easily processed and displayed, the electronic monitoring, displaying and storing of the electrocardiographic wave pattern has been addressed. Many patents deal with the detection, storage and display of the electrocardiographic wave pattern. Early efforts to visually display heart data were disclosed by Vogelman in U.S. Pat. No. 3,921,624. Shimoni in U.S. Pat. No. 4,617,938 and Citron in U.S. Pat. No. 4,417,306 disclosed systems for acquiring and recording electrocardiographic wave patterns. Further, Lisiecki disclosed a transfer of the recorded signals to a fixed computer for visual display. Anderson in U.S. Pat. No. 4,628,327 disclosed the acquisition, digitalization and storage of electrocardiographic wave patterns in a circular memory. Upon tripping of an alarm indicating a preset abnormal condition, the attached recorder rapidly produces a visual output of the stored data both before and after the event which tripped the alarm. Yoneda in U.S. Pat. No. 4,779,199 similarly disclosed acquisition and digitalization of the electrocardiographic wave pattern. Further, U.S. Pat. No. 4,115,864 and U.S. Pat. No. R 29,921 both disclosed the acquisition and storage of electrocardiographic wave pattern data followed by a display of that data with previously recorded electro cardiographic wave patterns to permit a visual comparison of the results by the physician.

As the above patents illustrate, most efforts at electronic storage and display of heart data have been directed to the electrocardiographic wave pattern. This is because the ECG wave pattern is much simpler and at a significantly lower frequency than the phonocardiographic heart sounds. Detection, digitization, storage and display of the phonocardiographic heart sounds are complicated by the presence of many other body sounds and by their higher frequency and more variable wave pattern. However, some work has been done in this area. Slavin in U.S. Pat. No. 4,483,346 disclosed a portable device for recording both an electrocardiographic wave pattern and phonocardiographic sounds. The phonocardiographic sounds were digitalized and stored for later transmission through a modem to a computer for storage and display. In U.S. Pat. No. 4,624,263, Slavin added cassette storage capability to the previously disclosed portable recorder. Further, Slavin disclosed the storage of abnormal phonocardiographic information for displaying with the patient's heart sounds to illustrate differences.

Although these devices may be useful for their intended purposes and may overcome some of the limitations of the classic air column stethoscope's dependence on the inherent energy contained in the original body sound, they do not address the issue that aural auscultation alone may not be sufficient to perform an adequate diagnosis, particularly of heart condition and are integrated into the chest piece or converting the conventional stethoscope into an electronic stethoscope.

Heart Failure—Congestive heart failure (CHF) is defined as impairment of systolic and/or diastolic function of the heart, leading to failure to meet the demands of peripheral tissues, or leading to maintenance of cardiac function under higher filling pressures.

In other words, CHF is a complex clinical entity that is characterized by ventricular dysfunction and compensatory neuron-hormonal alteration accompanied by exercise intolerance, fluid retention, and decreased life expectancy.

In CHF, the renin-angiotensin-aldosterone system and the sympathetic nervous system are considered to be of the utmost importance. These 2 interrelated systems regulate vascular tonus, heart rate, and contractility. CHF may stem from diastolic or systolic dysfunction.

In general, the 5-y mortality rate has been around 75% for men and 65% for women with CHF, whereas the 1-y mortality rate for severe and moderate forms of the disease reaches 40% to 50% and 15% to 25%, respectively. Coexistence of systolic and diastolic dysfunction is a frequent finding in CHF. Systolic dysfunction, in particular, is considered to be much more important in predicting the morbidity and mortality rates of the disease.

Echocardiographic evaluation of left ventricular ejection fraction (LVEF) obtained via the Simpson method has been an important parameter in the evaluation of systolic function, whereas atria-ventricular diastolic inflow waves have been obtained to assess diastolic function of the heart. Myocardial performance index (MPI) (Tei index) has been regarded as an important parameter in the evaluation of ventricular systolic function in congestive heart failure. MPI is defined as the sum of isovolumic relaxation time (IVRT) and isovolumic contraction time (IVCT) divided by left ventricular ejection time (LVET) ([IVRT+IVCT]/LVET). MPI is a Doppler-derived time interval index that combines both systolic and diastolic cardiac performance. The Tei index has been difficult to derive by using conventional non-Doppler pulsed echocardiography.

Therefore, it would be beneficial to have a versatile accessory to the conventional stethoscope that is easily portable, and has the capability to monitor and display at least heart sounds and heart electrical activity, as well as preserving the usual auscultation purposes of the conventional stethoscope that aids clinicians in diagnosing comprehensive heart issues.

BRIEF SUMMARY OF THE INVENTION

The present invention is the provision of a stethoscope front-end recorder device (also referred to as Sleeve) for the chest piece of a stethoscope, which is easily installed and removed. The Sleeve covers the circumference of the chest piece of a stethoscope. The Sleeve contains sensors for acquiring biosensor parameters such as electrocardiogram (ECG), body temperature, heartbeat, heart rhythm, heart rate variability (HRV), heart rate turbulence (HRT), heart sounds, respiration, heart murmur, heart rhythm, heart failure and blood flow. The Sleeve sensor system may be self-contained and does not require ancillary equipment to be connected or linked to the stethoscope to accomplish its utility.

In one embodiment, the current invention includes A method of determining an acoustic and electrical footprint of the heart comprising: (1) acquiring heart sounds and electrocardiogram, (2) transmitting the heart sound and the electrocardiogram to an acoustic stethoscope, (3) wirelessly transmitting the heart sound and the electrocardiogram to a mobile device, using a processor and wireless module, (4) the mobile device transmitting the heart sound and the electrocardiogram to a remote server, wherein the remote server analyzes both the heart sound and the electrocardiogram and determines cardiac malfunction, (5) transmitting the results to the mobile device and archiving the results after transmission, and (5) displaying on the mobile device the result of the analysis.

The current invention includes a system for determining normal and pathological heart sound comprising: (a) stethoscope front-end recorder device with biological sensors, wherein the front-end recorder device is configured to (a) acquire at least body sounds and electrocardiogram signals, (b) transmitting the at least body sounds and electrocardiogram signals to a client device and (c) display data transmission and battery life status.

The invention includes a client device configured to: display at least body sounds and electrocardiogram, enable a user to create or select patients, enable the user to select body sound location and electrocardiogram leads, record and review body sounds, electrocardiogram and cardiac index, transmit body sound and electrocardiogram signals to a remote server.

The invention includes remote server configured to: (1) analyze body sound and electrocardiogram for normal and pathological conditions, (2) authenticate the user, (3) archive body sounds, electrocardiogram and cardiac index.

One aspect of the invention is to provide a mobile system that monitors the electrical conductivity and the mechanical function of the heart for analyzing the entire cardiac cycle, wherein a user can track electrical deficiencies of the heart along with any abnormalities of the cardiac cycle, thereby detecting heart failure.

Another aspect of the invention is to provide a mobile system that monitors the cardiac cycle by analyzing the electrical conductivity and mechanical functions of the heart for heart rate. The mobile system measures the isovolumic contraction time (IVCT), isovolumic relaxation time (IVRT) and ejection time (ET), wherein a user abnormalities to the cardiac cycle that may be surrogate to heart failure and ejection fraction.

BRIEF DESCRIPTION OF THE DRAWINGS

In the following description embodiments of the object according to the invention is described with the help of the attached drawings.

DETAILED DESCRIPTION

Figure 1:
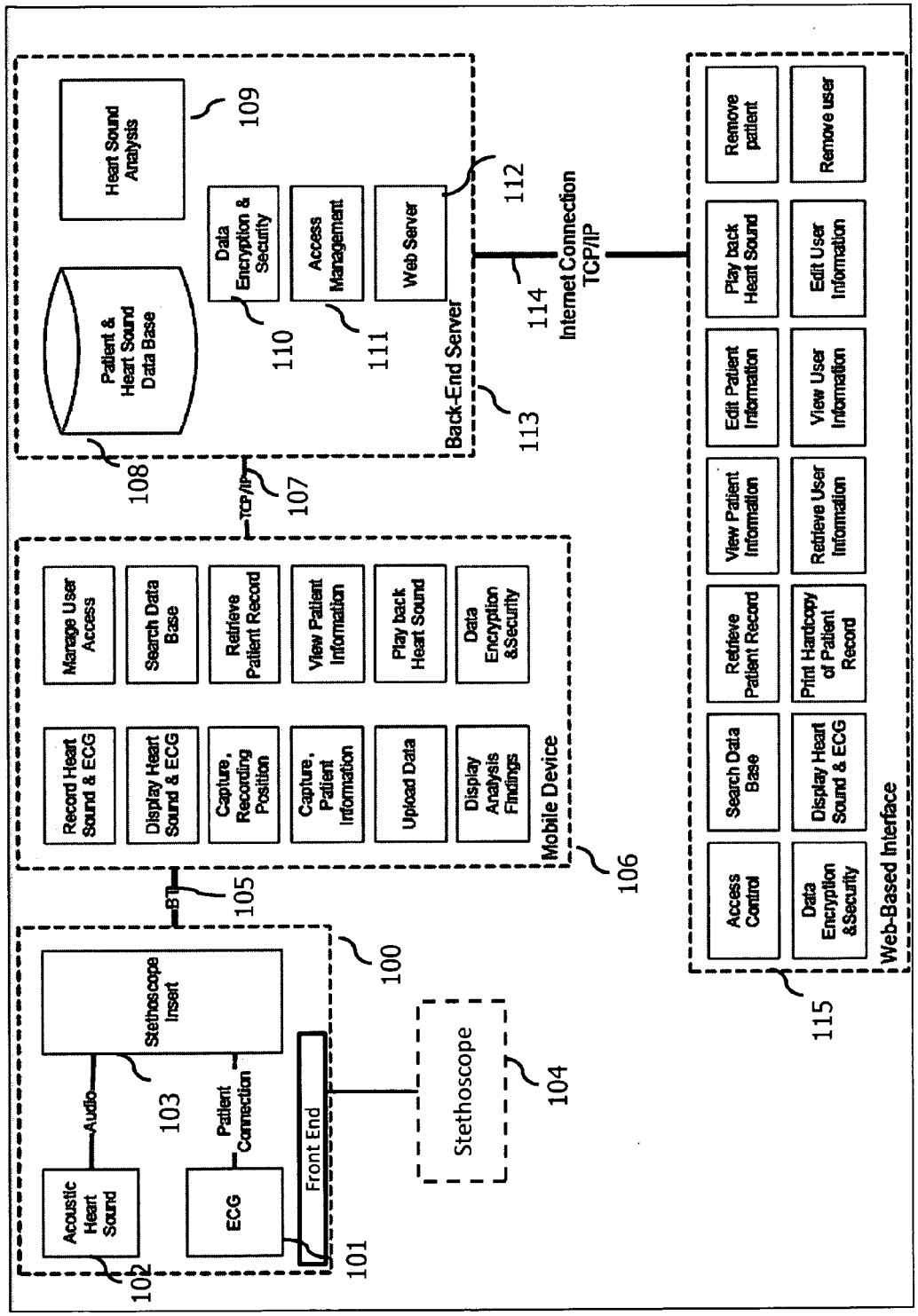
FIG. 1 illustrates a block diagram of the system and its components

The inventive system, in accordance to FIG. 1, consists of a stethoscope front-end recorder device 100 (also referred to as stethoscope recorder device or Sleeve) with a Bluetooth interface 105 connected to a standard acoustic stethoscope 104, a mobile device 106 with software component running on it, interfacing the stethoscope recorder device and a back-end server 113, with the capability to capture and save patient information to the backend server 113, as well as receiving analysis results and accessing stored patient information from the back-end server 113. A data processing unit on a back-end server 113 analyzes 109 the heart sound and ECG signal for pathological murmurs or only recording the ECG signal. The backend server 113 contains an encrypted database 108 for storing patient information. It also contains a web-server 112 and interface 115 for a user(s) to securely access patient data.

The sleeve interfaces with an acoustic stethoscope 114 and records both the acoustic heart sound 102 and/or ECG signals 101. In a preferred embodiment, those signals are sent via Bluetooth wireless communication protocol 105 to a mobile device 106. The sleeve can also communicate with the mobile device via wireless local area network (WLAN) products that are based on the Institute of Electrical and Electronics Engineers' (IEEE) 802.11 standards such as Wi-Fi. It can also use cellular network or mobile network. When the device's integral electrodes are placed on the chest of the patient, it is capable of verifying, measuring, storing and transmitting to a database the cardiac bio-potential activity.

Figure 2:
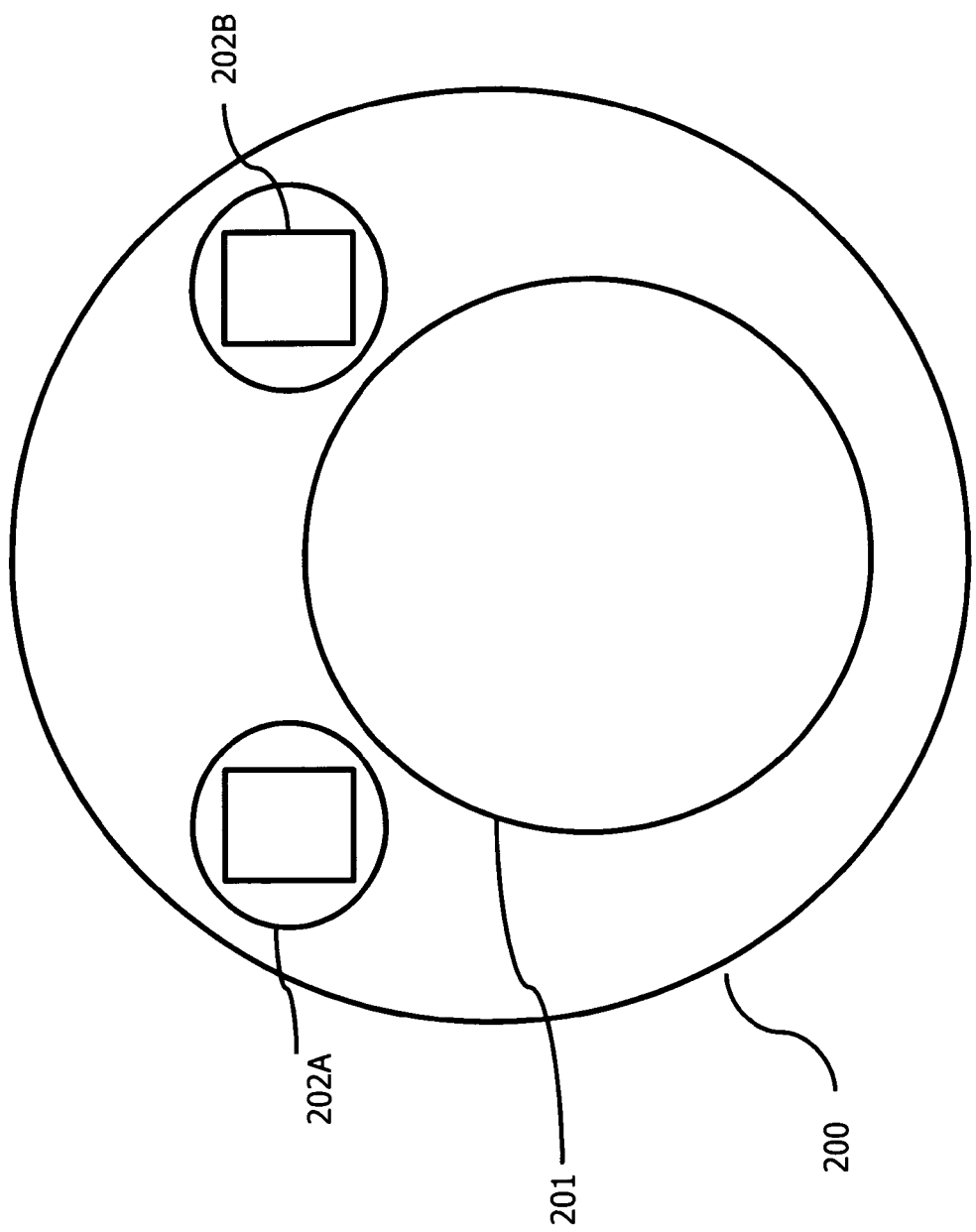
FIG. 2 illustrates the bottom view of the Sleeve
Figure 3:
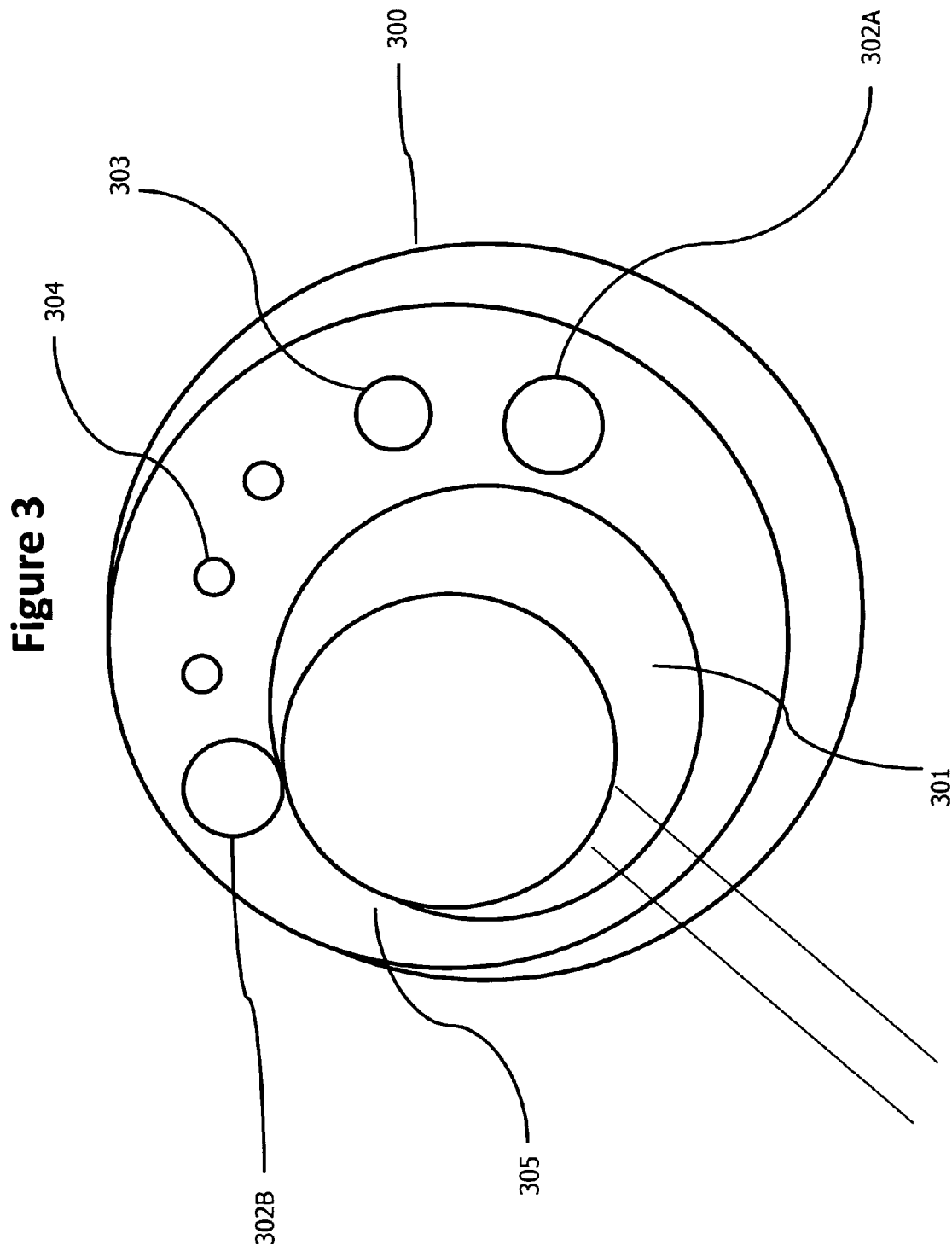
FIG. 3 illustrates a top view of the Sleeve

By using a cellular telephone or other client devices on which customized Sleeve software is installed to review physiologic data of a patient and to (a) view the near real-time waveforms remotely (b) remotely review other standard patient data. The Sleeve software can display at least the following physiologic data captured by the front-end recorder device:
  a) ECG Waveform
  b) Auscultation Waveform
  c) Cardiac Index
  d) Systolic Blood Pressure Cuff
  e) Diastolic Blood Pressure Cuff Referring to FIG. 3, the sleeve 300 covers the circumference or the outer edge of a conventional stethoscope 301 applied to the diaphragm of stethoscope 405 of FIG. 4. The sleeve 300 is held in place on the chest piece of the stethoscope by a flexible, stretchable skirt 305 extending to the edge the circumference of the stethoscope's bell 301. The sleeve has a thickness of at least 0.5 inch. The circumference of the sleeve contains at least 2 ECG electrodes obtaining 202A and 202B of FIG. 2 signals and a diaphragm 201. The ECG electrodes enable the user record ECG Lead I, Lead II and Lead III, by rotating the negative and positive electrodes around the patient's chest, using einthoven's triangle vector theory, similar to what taught in U.S. Pat. No. 6,884,218 (incorporated by reference).

Figure 4:
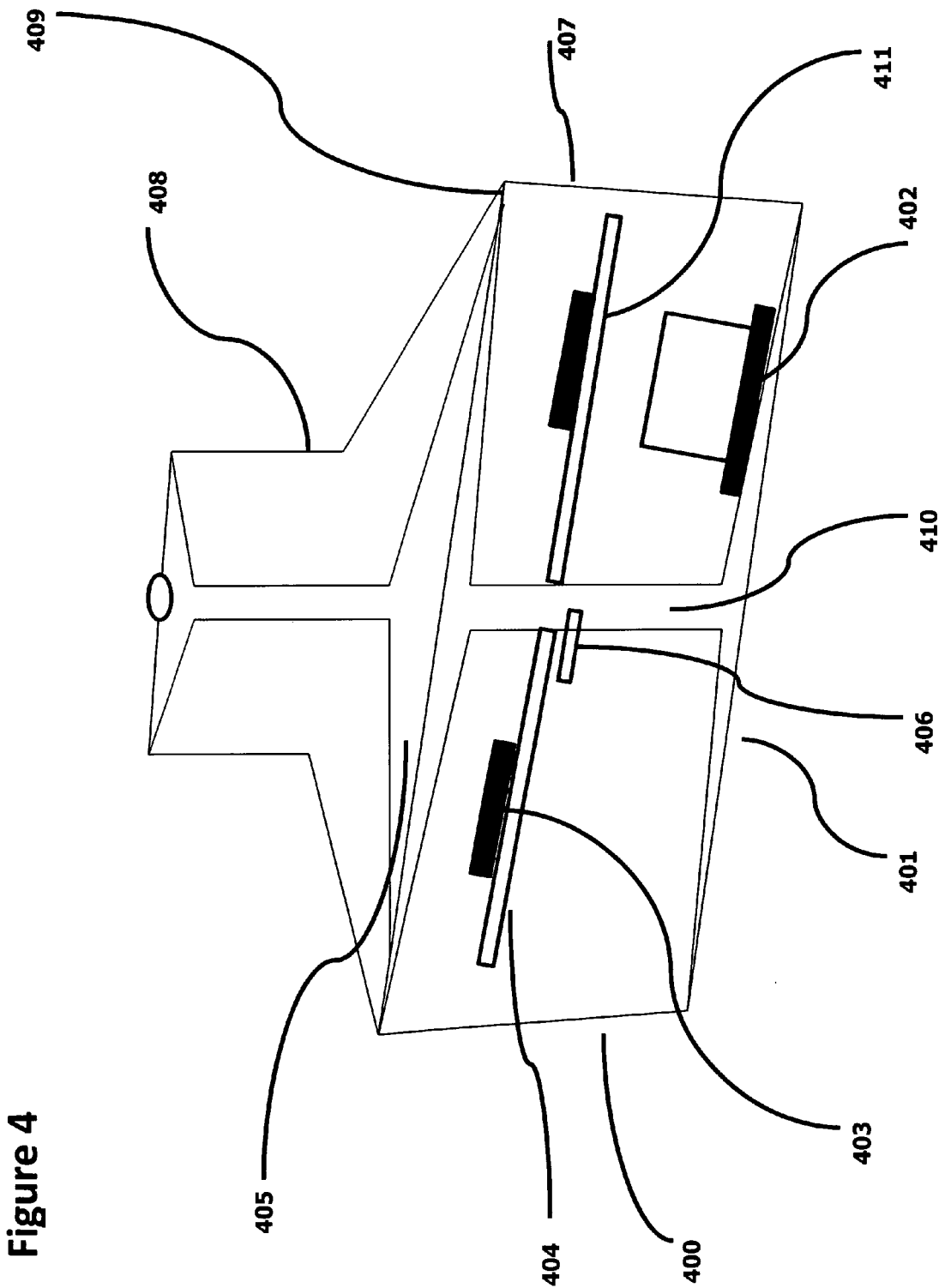
FIG. 4 illustrates a cross section of the Sleeve
Figure 5:
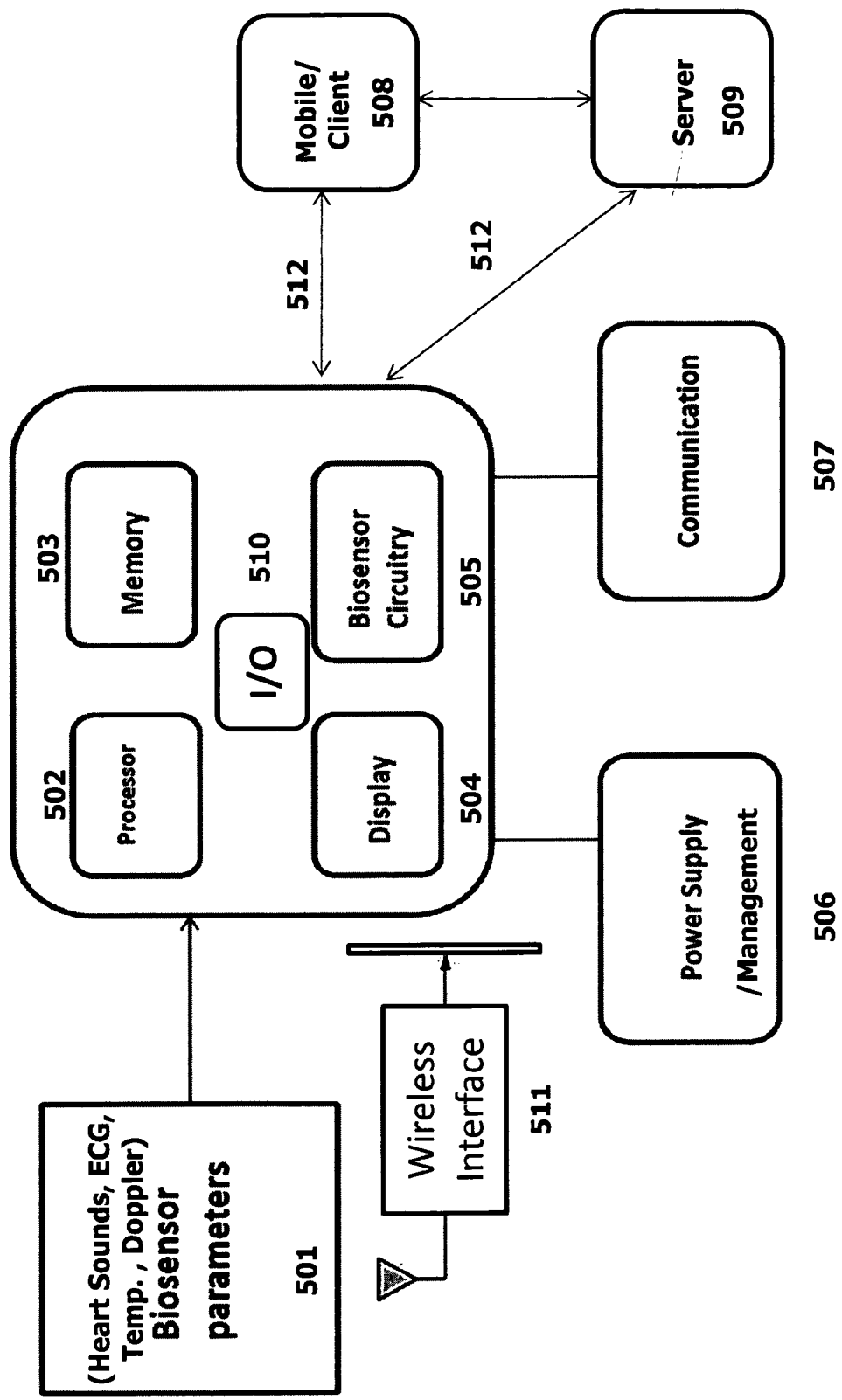
FIG. 5 illustrates a block diagram of the electrical components

Referring to FIG. 4, the sleeve 400 contains printed circuit board, or PCB 404 and an optional display module (not shown) in an enclosure box 400. The PCB 404 contains electronics circuitry that comprises a processor 403 and the corresponding circuitries for biosensor parameters 501 of FIG. 5. Referring to FIG. 5, the PCB contains a computer processing unit (CPU) 502 with memory 503, an input/output (I/O) circuit 510, and an optional view screen 504. A power supply 506 is in operative communication with the circuits of the display and processing modules to provide electrical power as needed. The electric signal inputs from to the sensors (e.g., ECG, temperature, and microphone) are inputted via the electrode connector of the sensor sleeve. The sensor circuitries further condition and digitize the biosensors parameters from the sensor sleeve. The digitized signals are then conducted under the control of the CPU and memory circuits to the view screen display for visual display, or to the I/O and communication ports for export from the PCDM to client devices (e.g., mobile, pc or remote server, printers, data storage devices, signal display equipment and other devices). The Sleeve contains light-emitting diodes 304 of FIG. 3 (LEDs) as indicators to communicate different modes such as on/off, data transfer, and battery indicator. The Sleeve also includes a power switch 303, and negative/positive indicators 302A and 302B. The Sleeve also contains 2.5 mm headphone port for output body sounds to headphone or speakers. Alternatively, the captured heart or body sound may be output to a speaker or sound exciter, used to enhance the sound signal going to stethoscope.

In a preferred embodiment, the power supply is a rechargeable power supply, and more particularly, a rechargeable battery 402 of FIG. 4 power supply. In the preferred embodiment, the battery or batteries of the power supply is rechargeable lithium polymer battery.

The CPU processor comprises a tangible medium, for example read only memory (ROM), electrically erasable programmable read only memory (EEPROM) and/or random access memory (RAM). The processor may comprise many known processors with real time clock and frequency generator circuitry, for example the PIC series of processors available from Microchip, of Chandler Ariz. In some embodiments, processor may comprise the frequency generator and real time clock.

The processor can be configured to control a collection and transmission of data from the ECG, microphone, accelerometer and temperature circuitries. In another embodiment, the processor may be configured to collect data from a pressure transducer for nasal airflow. In other embodiments, the processor may be configured to collect data from a blood pressure monitor, pulse oximeter, electromyogram (EMG), Doppler and ultrasound.

The PCB 404 also comprises of wireless communication circuitry 511 of FIG. 5, communication module coupled to the processor system to transmit the biosensor parameters to client devices 508 (mobile or personal computer) or remote server 509 with a communication protocol 512. The communication protocol may comprise at least one of Bluetooth, Zigbee, WiFi, WiMax, IR, a cellular protocol, amplitude modulation or frequency modulation. The client devices may comprise a data collection, analysis and display systems to collect and/or store data from the wireless transmitter and wherein the data collection system is configured to communicate periodically with the remote center and the Sleeve with wireless connection and/or wired communication. In some embodiments, the sleeve sensor device may have a rechargeable module, and may use dual battery and/or electronics modules, wherein one module can be recharged using a charging station while the other module may be a tiny USB port placed on the sleeve sensor.

Figure 5A:
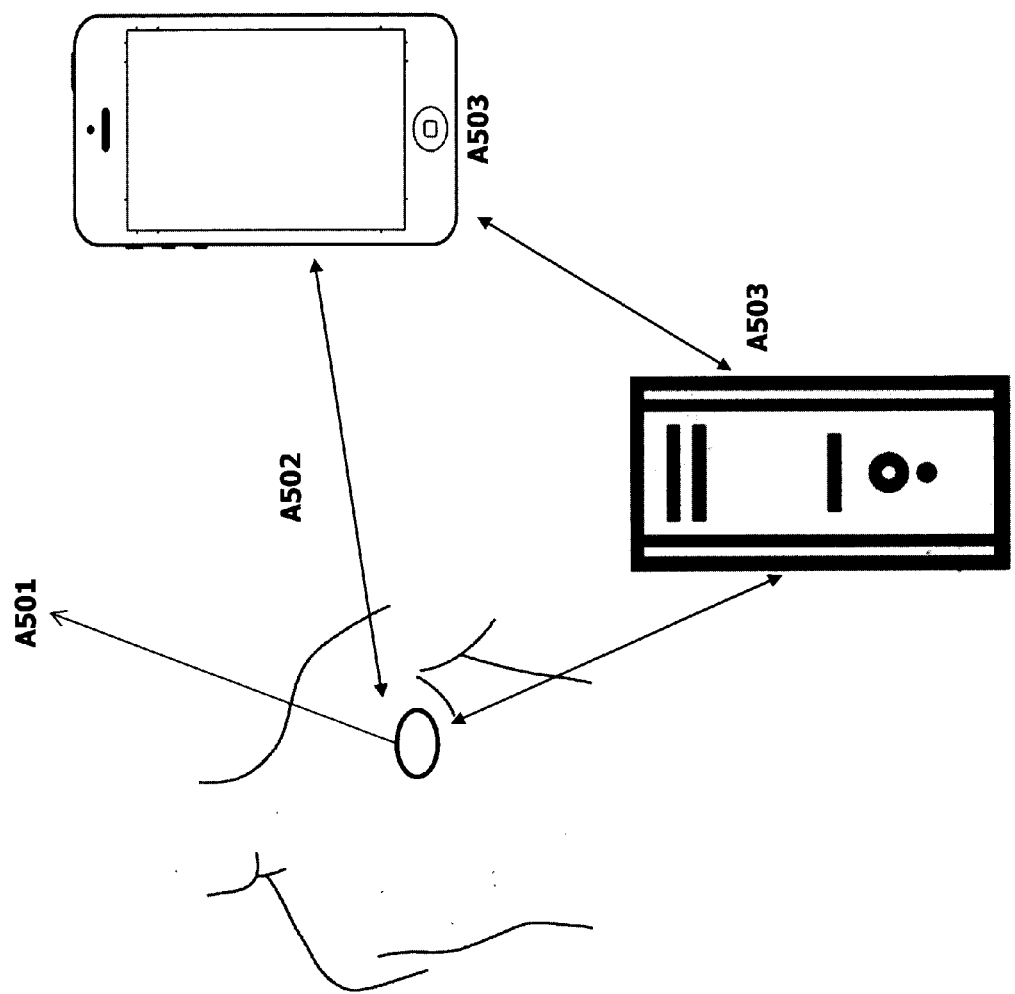
FIG. 5A Illustrates an interaction between a self-contained Sleeve, Mobile device and server FIG. 6 Illustrates Server, Network, Client Devices and Sleeve interaction

Referring to FIG. 5A, in another embodiment, the sensor sleeve A501 may be self-contained unit affixed and/or adhered to the body of the patient or user. For example, the sensor sleeve may be affixed and/or adhered to the body with at least one of the following: an adhesive tape, suspenders around shoulders, a pre-shaped electronics module to shape fabric to a thorax, a pinch onto roll of skin, or transcutaneous anchoring. The sleeve sensor may also adhere to the body via a chest strap, and/or a low-irritation adhesive for sensitive skin. In addition to having a circular shape, the sensor device can be comprised of many shapes, for example at least one of an hourglass, an oblong, a circular or an oval shape. The sleeve sensor may comprise a reusable electronics FIG. 5 module with replaceable cover, and each of the replaceable covers may include a battery. The sleeve sensor electronics may comprise of a module for collecting biosensor data for approximately at least 1 day, with the capability to wirelessly send data to a client device via Bluetooth, Zigbee, WiFi, WiMax, IR, a cellular protocol, amplitude modulation or frequency modulation or wired via Universal Serial Bus (USB) and proprietary connectors. The entire sleeve sensor and electronics component may be disposable. In some embodiments, the sleeve sensor device may have a rechargeable module, and may use dual battery and/or electronics modules, wherein one module can be recharged using a charging station while the other module may be a tiny USB port placed on the sleeve sensor.

The bottom of the sleeve contains a diaphragm 401 in FIG. 4. When the diaphragm is placed against the patient, the sounds of the body vibrate the plastic disk and acoustic pressure waves are formed. These pressure waves travel up the sound chamber 401, delivering body sounds to the bottom of the user's stethoscope 405, which is attached to the lid of the sleeve 407.

Running on the backend server 113 is heart sound analysis software 109 that assists medical examiners in analyzing cardiac sounds for the identification and classification of suspected murmurs. It is used to distinguish between normal/physiological and pathological heart murmurs by recording the acoustic signal of the heart and the ECG signal simultaneously and analyze these signals. The acoustic heart signal is analyzed to identify specific heart sounds that may be present.

Figure 6:
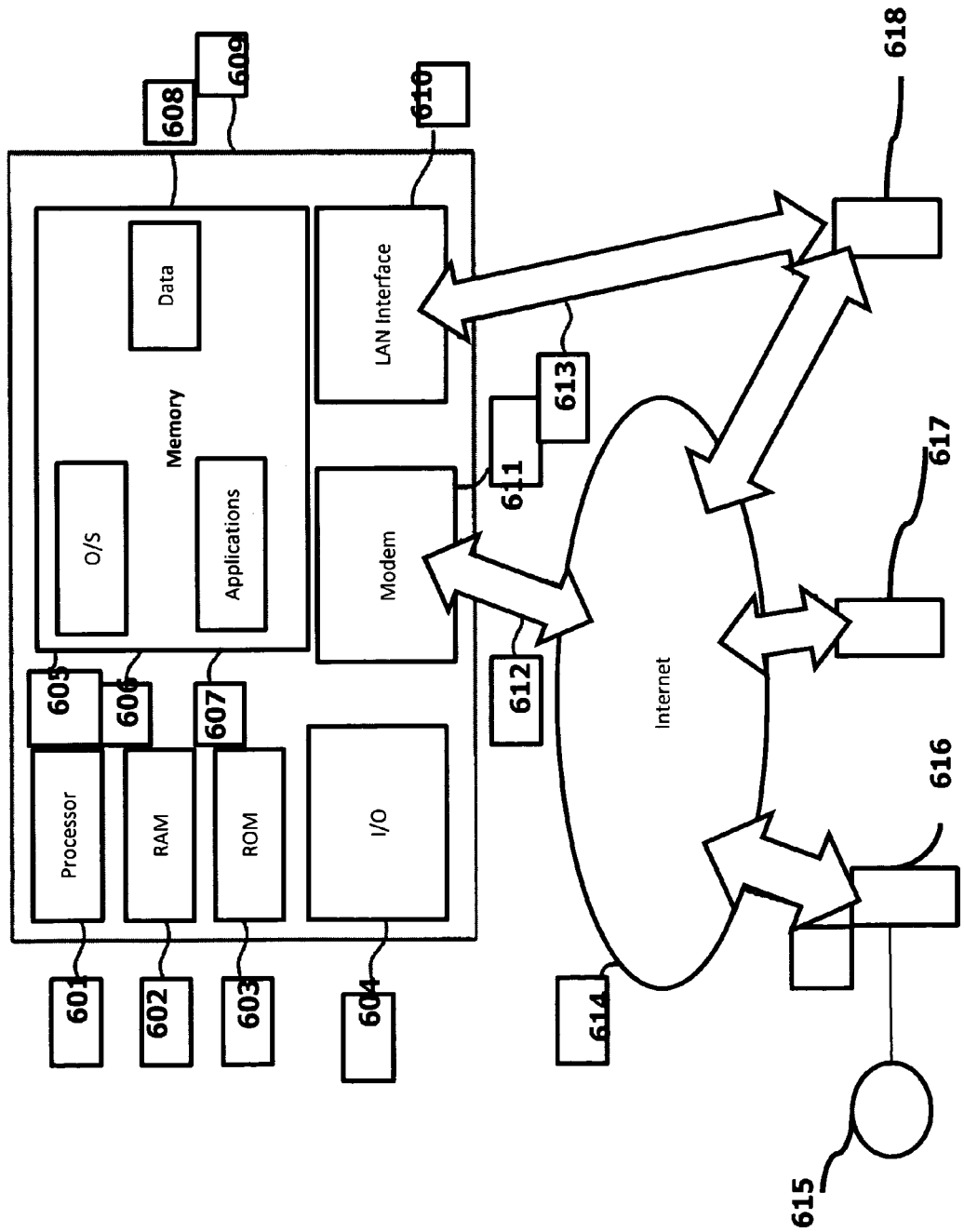

FIG. 6 illustrates a block diagram of a generic computer server 309 that may be used according to an illustrative embodiment of the invention. The computer server 309 may have a processor 601 for controlling overall operation of the server and its associated components, including RAM 602, ROM 603, input/output module 604, and memory 605.

I/O 604 may include a microphone, keypad, touch screen, and/or stylus through which a user of device may provide input, and may also include one or more of a speaker for providing audio output and a video display device for providing textual, audiovisual and/or graphical output. Software may be stored within memory 605 and/or storage to provide instructions to processor 604 for enabling server 609 to perform various functions. For example, memory 605 may store software used by the server 609, such as an operating system 606, application programs 607, and an associated database 608. Alternatively, some or all of server 609 computer executable instructions may be embodied in hardware or firmware (not shown). As described in detail below, the database 608 may provide centralized storage of account information and account holder information for the entire business, allowing interoperability between different elements of the business residing at different physical locations.

According to certain aspects, the server 609 may operate in a networked environment supporting connections to one or more remote devices, such as client devices 616, 617, 618 (cell phone, PC, laptop and tablets) via the internet 614, communicating with the Sleeve 615. The communication network in this example may be connected to an Internet router via a Local Area Network (LAN) network 613 or Wide Area Network (WAN) 612, and may receive electrical power via a supplied AC power adaptor.

Figure 8:
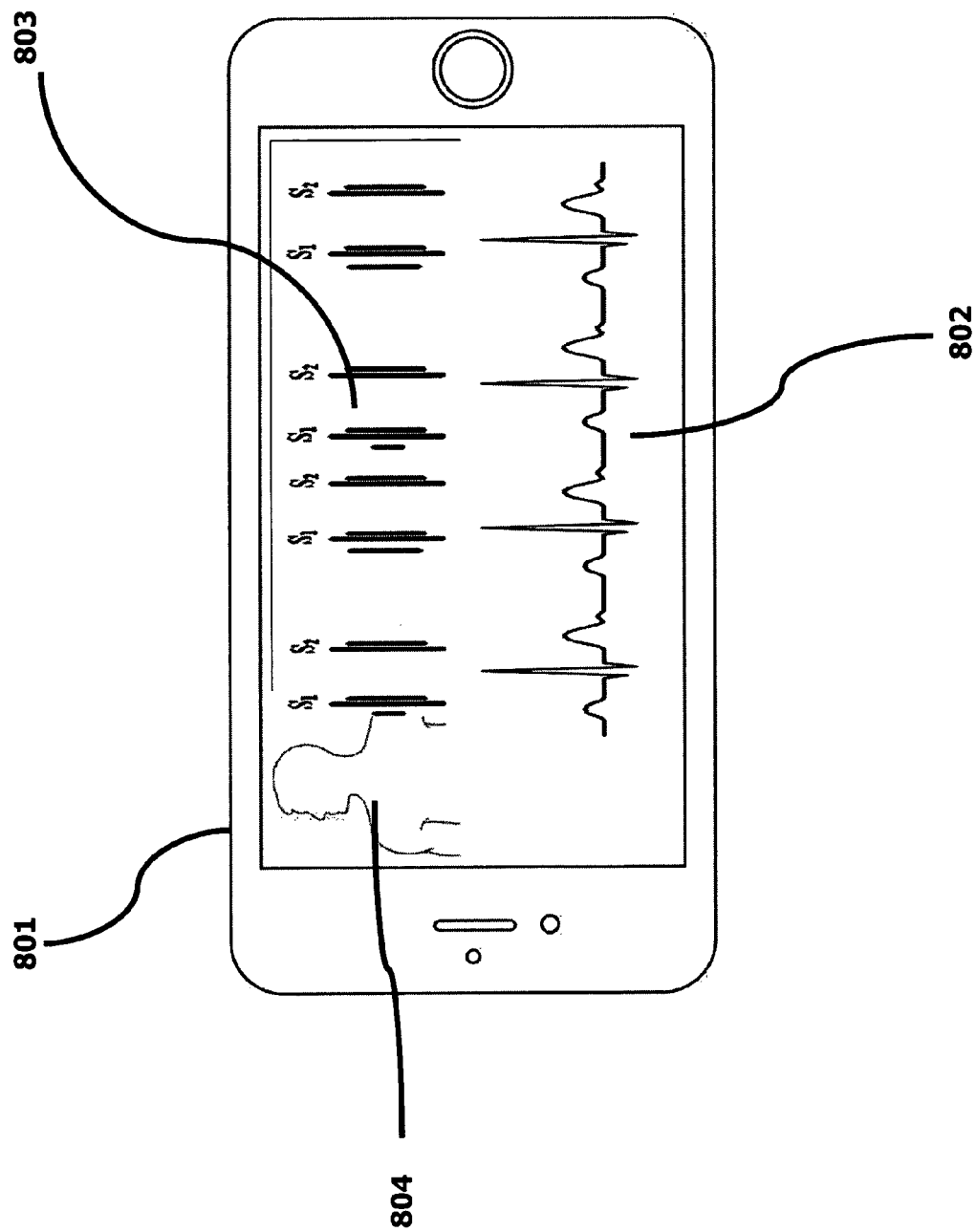
FIG. 8 illustrates a mobile client device
Figure 9:
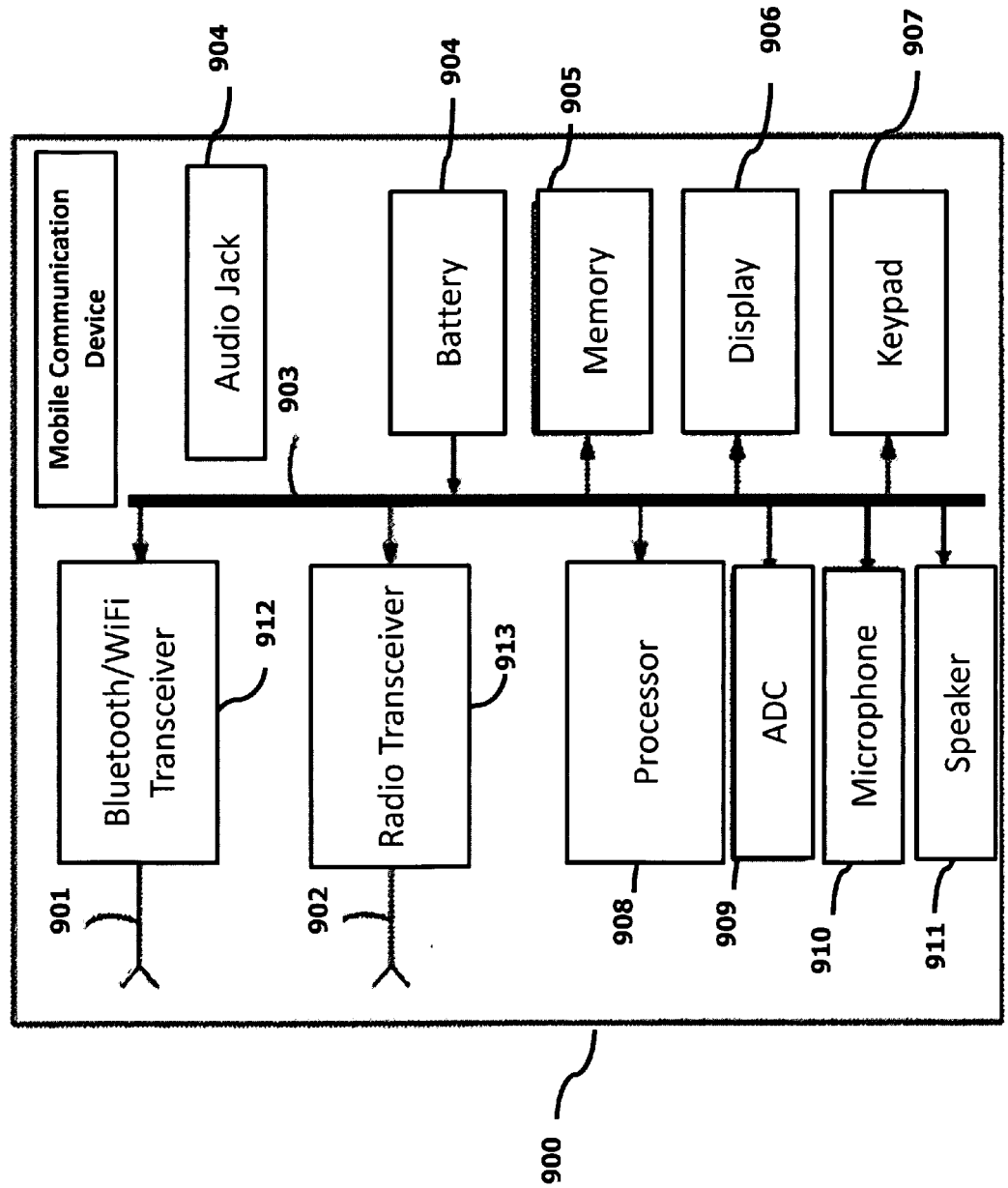
FIG. 9 illustrates a block diagram of the mobile client device

Referring to FIGS. 8-9, the sleeve software application is installed on a mobile device 801. The software component running on a mobile device, interfaces with the stethoscope recorder device and the back-end server, with the capability to capture and save patient information to a back-end server, as well as receiving analysis results and accessing stored patient information from the back-end server.

In a preferred embodiment, the mobile device 801 interfaces via Bluetooth 105 with the sleeve device to capture the acoustic heart sound and/or ECG signals on a mobile device and manage this connection. The mobile device sequences the recording of the acoustic heart sound and ECG signals at the various recording locations between the Sleeve front-end and mobile device.

FIG. 9 is a block diagram illustrating selected elements of the mobile communication device 900 in accordance with some embodiments. A processor 908 is coupled to a wireless radio transceiver 902, a display 906, a keypad 907, and a memory 905. The radio transceiver 901 is connected to an antenna 902, which is an example of an antenna and is adapted to send outgoing voice and data signals and receive incoming voice and data signals over a radio communication channel. The radio communication channel can be a digital radio communication channel (e.g., a cellular channel as provided by a cellular service provider), such as a CDMA or GSM channel such a radio communication channel has the capacity to communicate both voice and data messages using conventional techniques. In some embodiments, the processor 908 also is coupled to a second Wireless transceiver 901 (e.g., a Bluetooth or WiFi transceiver), connected to a corresponding antenna 902, for communicating with the Sleeve or server.

The processor 908 has the capability to perform not only the radio communication services necessary to allow for phone and data communications (e.g., via the transceivers 901 and/or 902), but also to execute various application programs that are stored in the memory 905. These application programs can receive inputs from the user via the display 906 and/or keypad 907. In some embodiments, application programs stored in the memory 905 and run on the processor 908 are, for example, iPhone, Android, Windows Mobile, BREW, J2ME, or other mobile applications and can encompass a broad array of application types. Examples of these applications include medical applications games, and multimedia applications. Medical applications can include the Sleeve's decision support software package to assist the medical examiner during heart auscultation to distinguish between normal/physiological and pathological heart murmurs by recording the acoustic signal of the heart and the ECG signal and analyze these signals.

Referring to FIG. 8, the mobile device 801 displays the acoustic heart sound 803 and/or ECG signals 802 on the mobile device while recorded from the Sleeve. It captures, displays, and uploads patient information and the recorded signals to the backend server (encrypted). The mobile device displays heart sound analysis findings on the mobile device (in-time) or possible error messages generated by the back-end processing unit. It retrieves and display patient information from the back-end server on the mobile device. The user also saves and archives patient data, heart sound and/or ECG recordings on a back-end server (secure and encrypted), using the mobile device.

Figure 7:
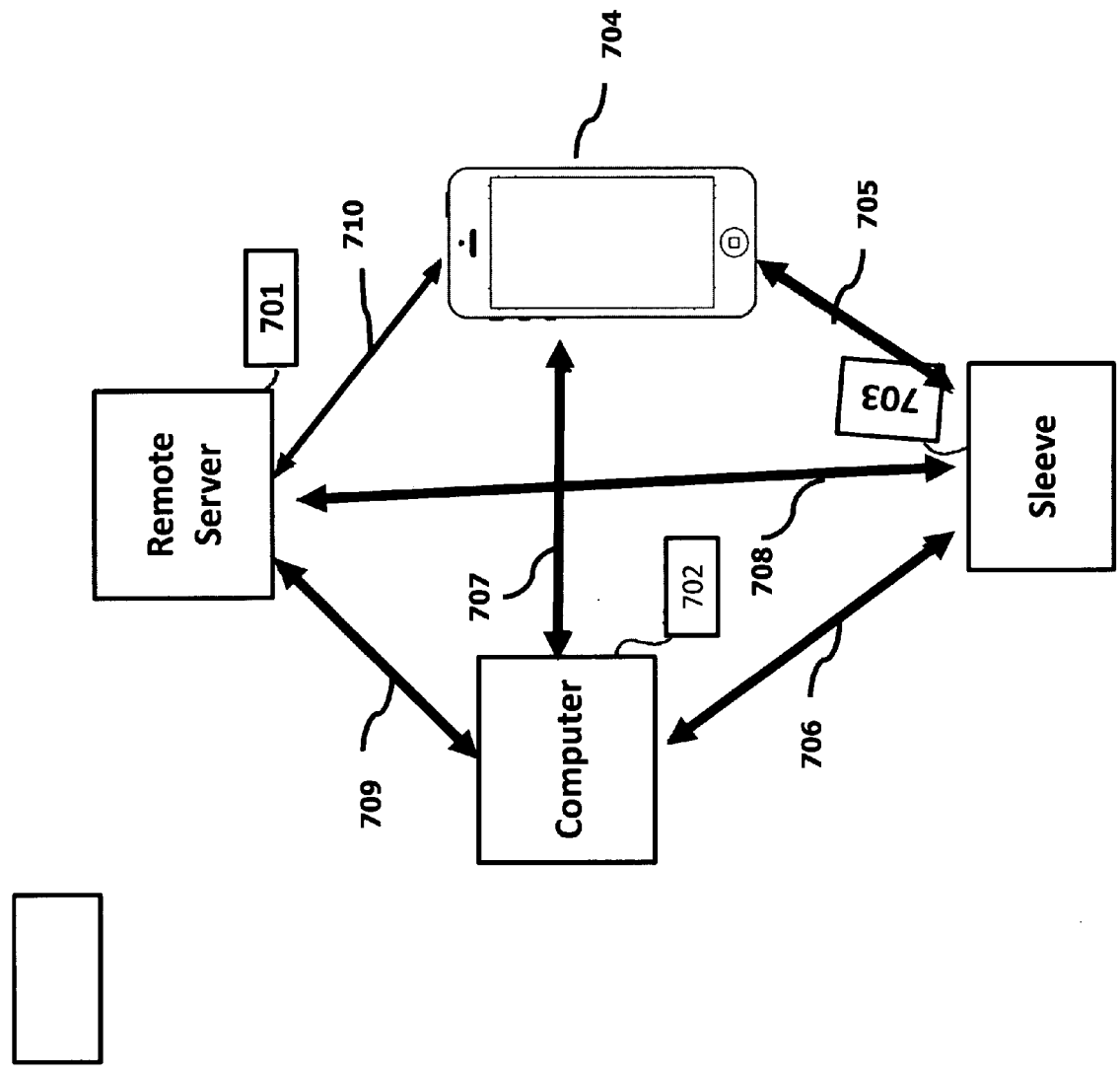
FIG. 7 illustrates how the devices are connected to each other

FIG. 7 shows the interaction between the devices. For purposes of this disclosure, local computer 702 and mobile device 704 are defined to include all computing devices, whether portable or stationary. This definition includes, but is not limited to, electronic books, laptop and handheld computers, cellular phones, pagers, desktop computers, personal digital assistant (PDA), telehealth gateway or hub and wearable computers. The Sleeve 703 interconnects with the remote health server 701. The Sleeve 703 may communicate with web applications running on the remote server 701 via the Internet or a private network 708. The Sleeve may include cellular, WiFi other wireless or wired communication capability so as to interconnect with the server 701 either continuously or periodically. Communication with the remote server 701 may be via the local computer 702 or mobile device 704. The Sleeve 703 may also include some type of memory chip or memory module that may be removed and inserted into the local computer 702 or the mobile device 044 for transfer of data. The Sleeve 703 may communicate with local computer 702 by interconnecting a wire between the computer 702 and the Sleeve 703, or by "docking" the Sleeve 703 into a communications dock associated with computer 702. The Sleeve 704 may also communicate with the computer 702 and a mobile device 74 by wireless communication 706, 705, such as infrared communication, Bluetooth and Zigbee or with a wired connection such as USB (Universal Serial Bus). The computer 702 and mobile device 704 communicates with the remote server 701 by cellular, WiFi other wireless or wired communications.

Figure 14:
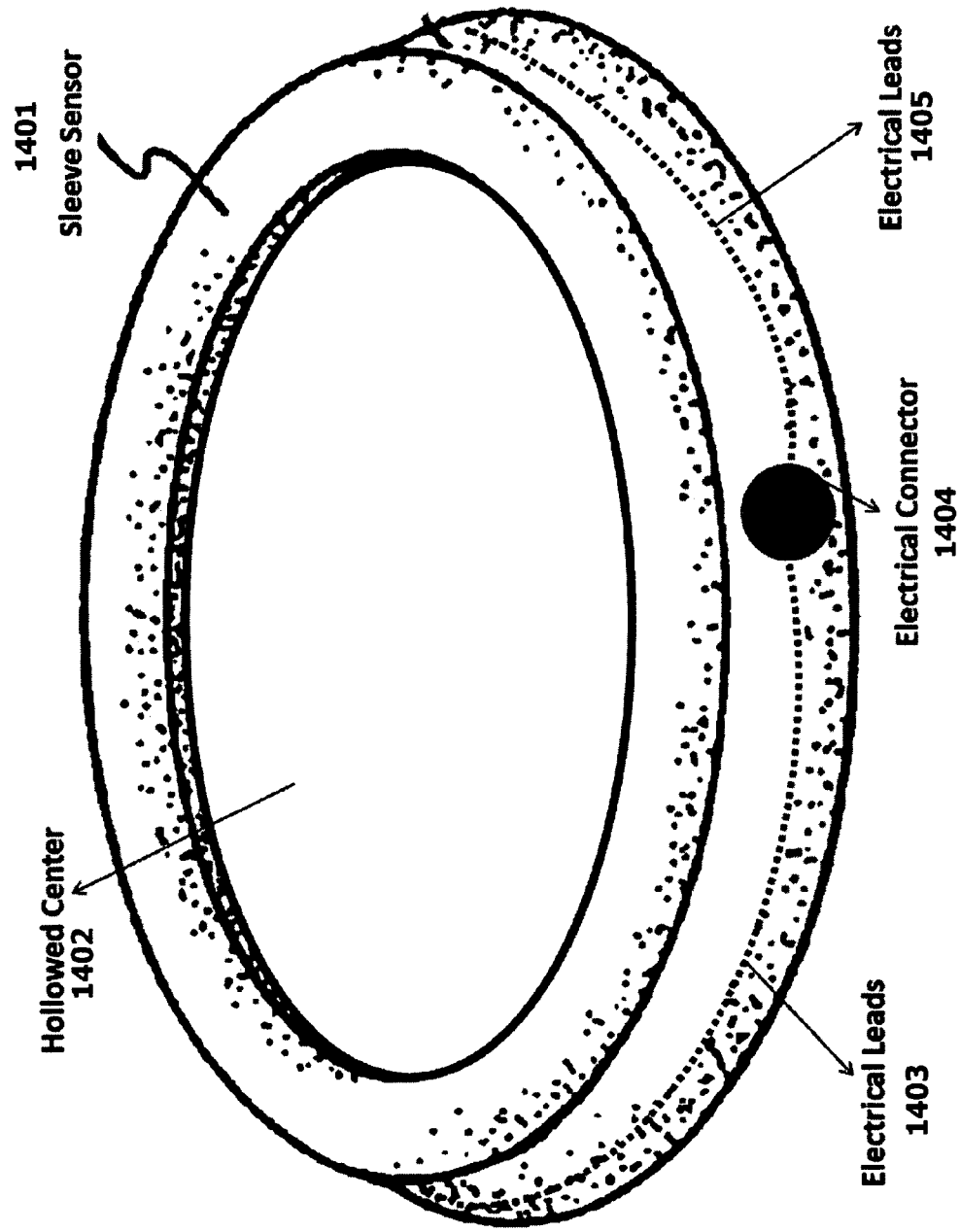
FIG. 14 illustrates an alternative ring Sleeve
Figure 15:
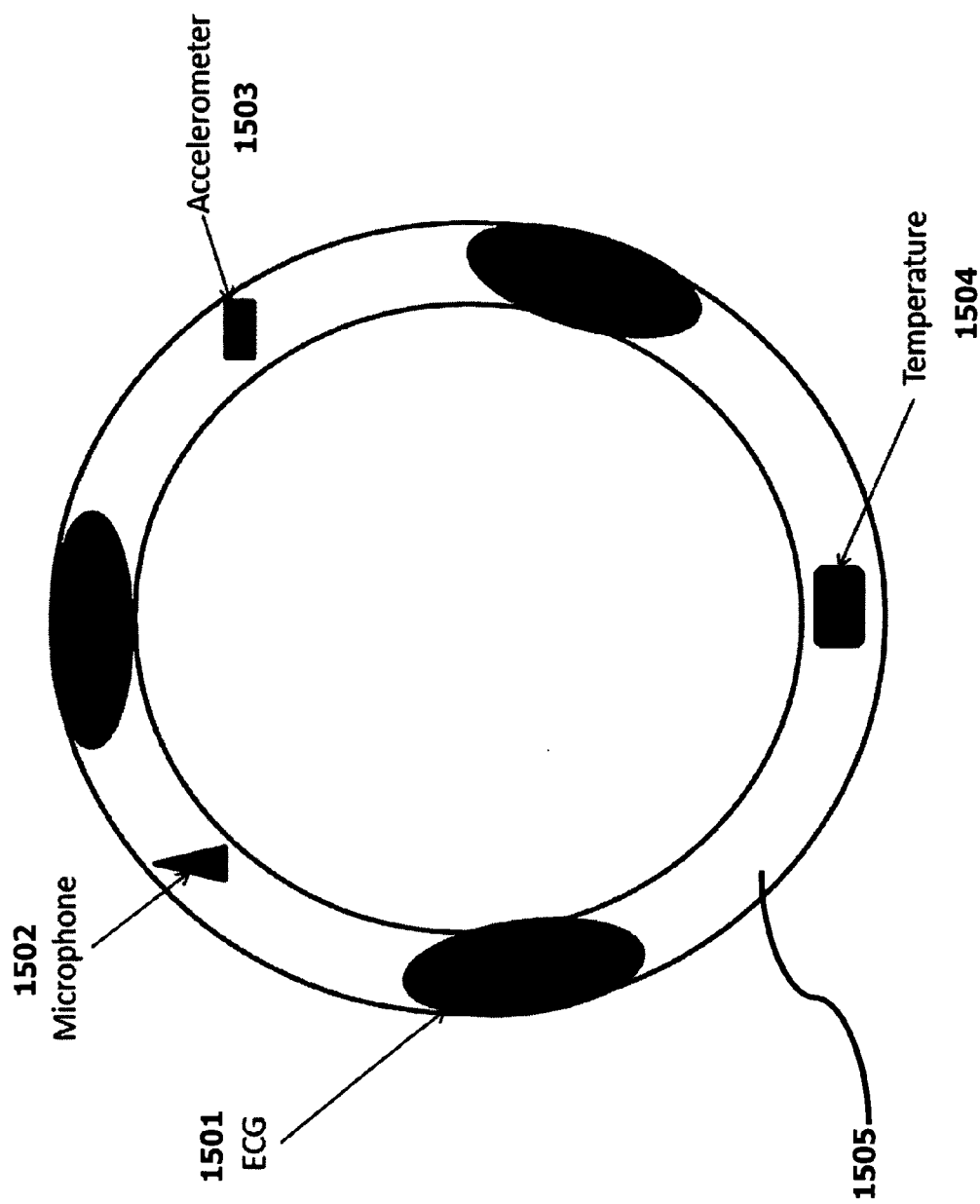
FIG. 15 illustrates the alternative ring Sleeve with Sensors

Referring to FIG. 15, in another embodiment, the circumference of the sleeve 1505 contains at least one microphone 1502 (e.g., electret, Micro-electromechanical systems (MEMS) or micro or piezoelectric transducer capable of low frequency response applied to body surface) used to record a body sounds. The circumference of the sleeve also contains a temperature sensor to record body temperature 1504, and an accelerometer 1503. In many embodiments, the accelerometer comprises at least one of a piezoelectric accelerometer, capacitive accelerometer or electromechanical accelerometer. The accelerometer 1503 may comprise a 3-axis accelerometer to measure at least one of an inclination, a position, an orientation or acceleration of the patient in three dimensions. Accelerometer can be used to provide respiration rate and blood flow for the patient. The above sensors have electrical leads attached to them, running along the body of the sleeve, coming together to form at least one electrical connector 1403, 1405 in FIG. 14. Any polymer or metal capable of being formed into a light weight, flexible sheet is suitable for the sleeve sensor. The preferred materials are polyolefin and silicon rubber. Useful polyolefins include polyethylene, polypropylene, polyvinyl chloride, and copolymers thereof. The sensor sleeve can also be made out of any other flexible and stretchable materials or a combination of flexible and rigid materials. The ECG electrodes are pieces of conductive material.

Figure 10:
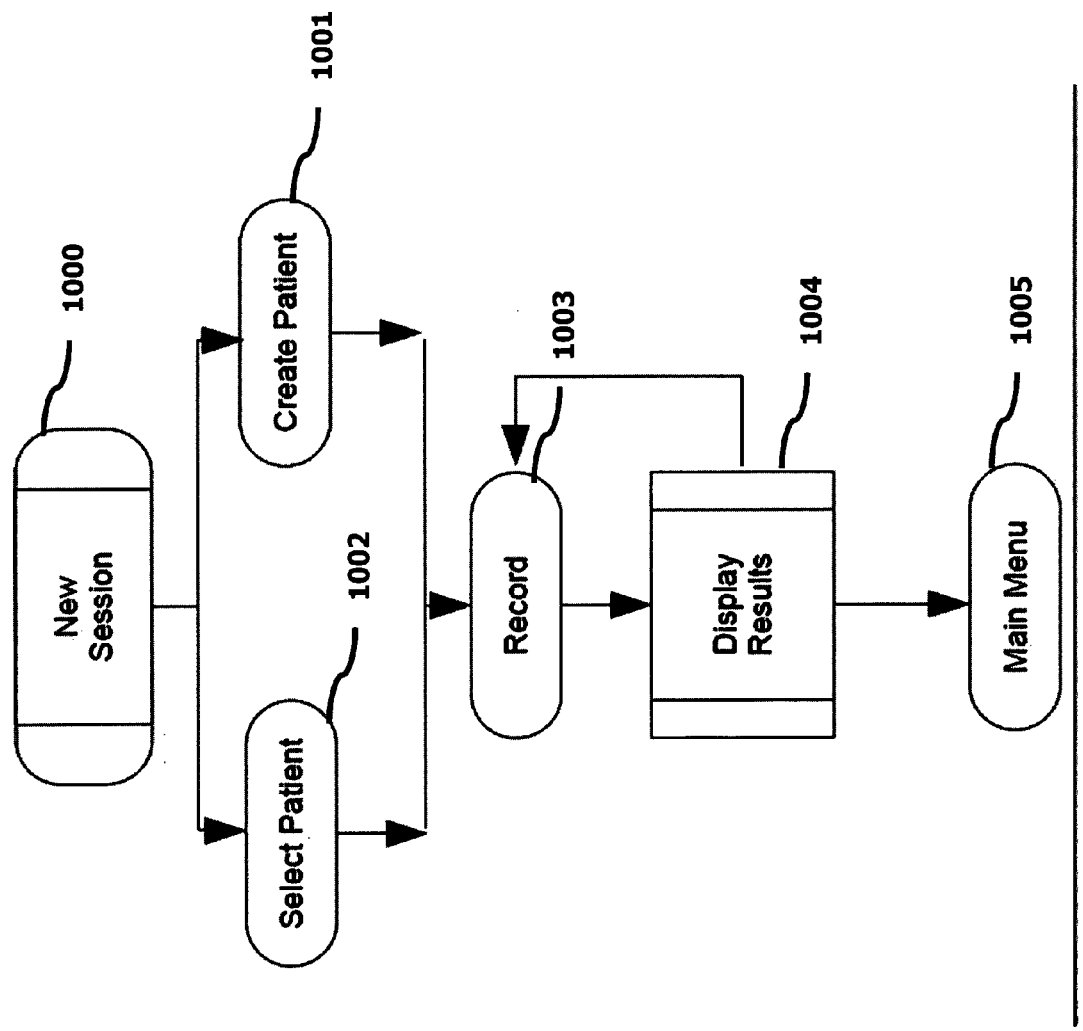
FIG. 10 illustrates a new session creation

Referring to FIG. 10, the user selects a new session, 1000 and creates 1001 or selects 1002 new patients using the custom software running on the client device. New patients are created by entering patient information such as Name, patient ID, Birth Date, Gender, Weight, Contact details, Session, Systolic blood pressure, Diastolic blood pressure and Height (this list is not intended to be exhaustive). Once a patient is selected user can start recording heart sound and or ECG 1003. After recording, the results can be displayed 1004 to the user. User can go back to the main menu 1005 for recording option or review results.

Figure 13:
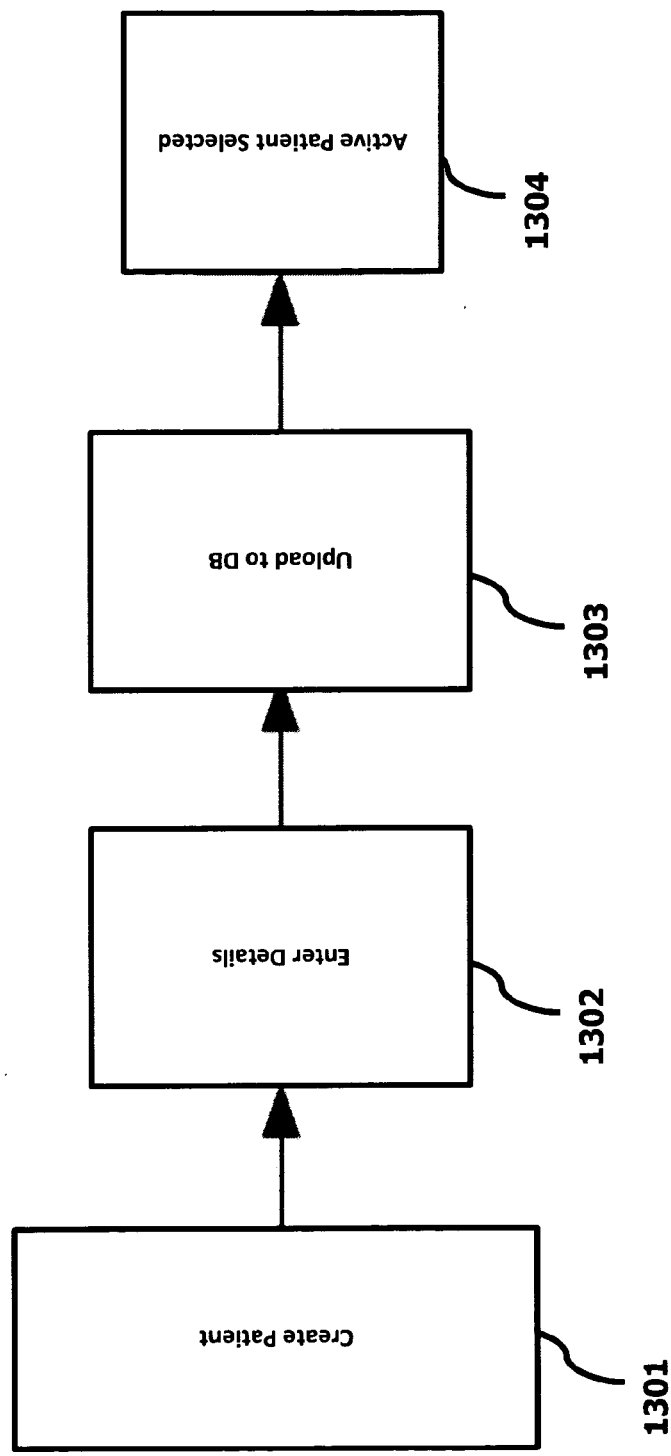
FIG. 13 illustrates the creation of new patients

FIG. 13 also teaches the aspect of creating a patient 1301, by entering patient information or details 1302, using a client device. Patient details are uploaded to patient database 108 in FIG. 1 at the backend server 113 in FIG. 1. Once patient details are uploaded, the patient is activated for selection 1304.

Figure 11:
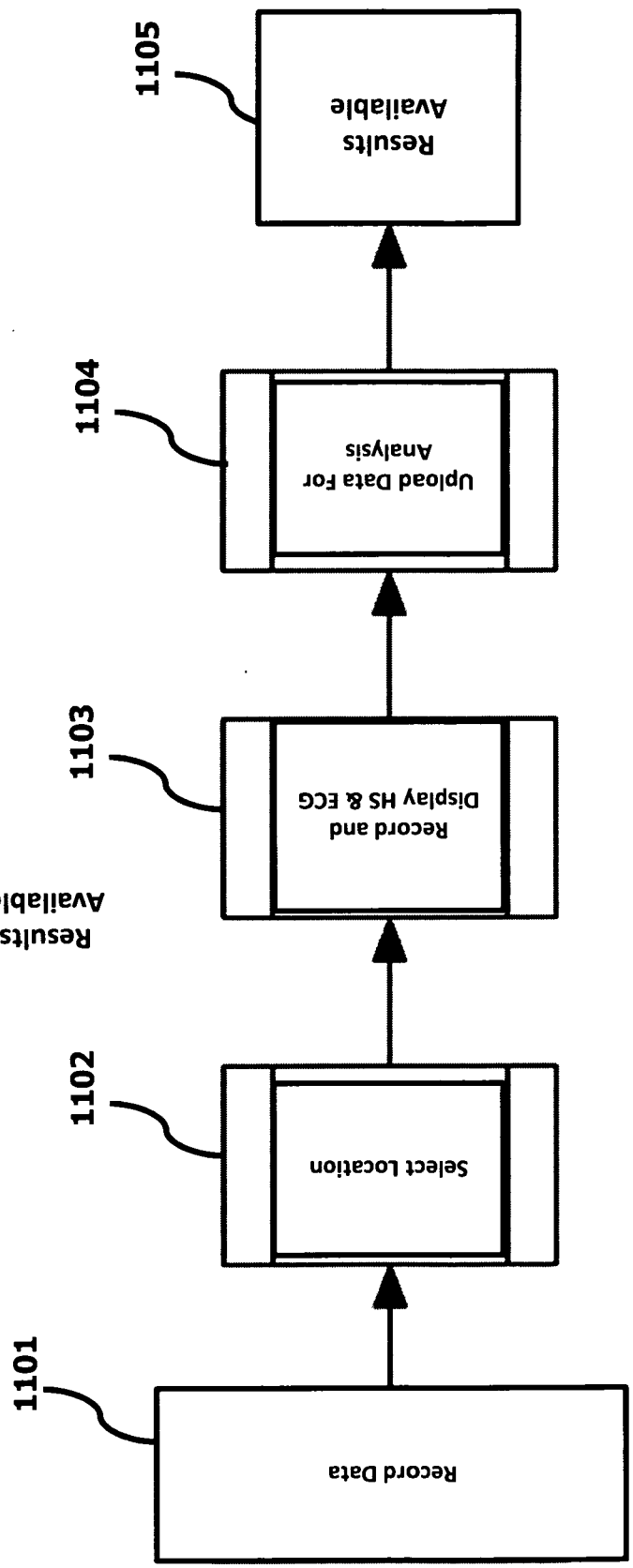
FIG. 11 illustrates a recording session

Referring to FIG. 11, the user goes to the process of recording 1001 physiological parameters (such as heart sound and/or ECG) by selecting or creating a patient. For heart sound, once a patient is selected, user selects auscultation location 1102 (Tricuspid, Aortic, Pulmonary, Apex (mitral)). User chooses patient posture by selecting Sitting, Standing or Supine. User also sets recording duration (e.g., 10 to 30 seconds). Then, user records at least hearts sounds and ECG 1003. In this case, the user is a health care worker or physician. Continuous streaming heart sounds and or ECG from the Sleeve (Bluetooth) is enabled when user taps onto the auscultation spot 804 in FIG. 8 (Aortic, Pulmonary, Tricuspid and Mitral), illustrated by a chest on the application, and initiate the recording for that particular position. The user can tap on the same position to discard the recording. Results are uploaded to server for analysis 1104. After analysis, results are available 1105 and transmitted to the client device.

Figure 12:
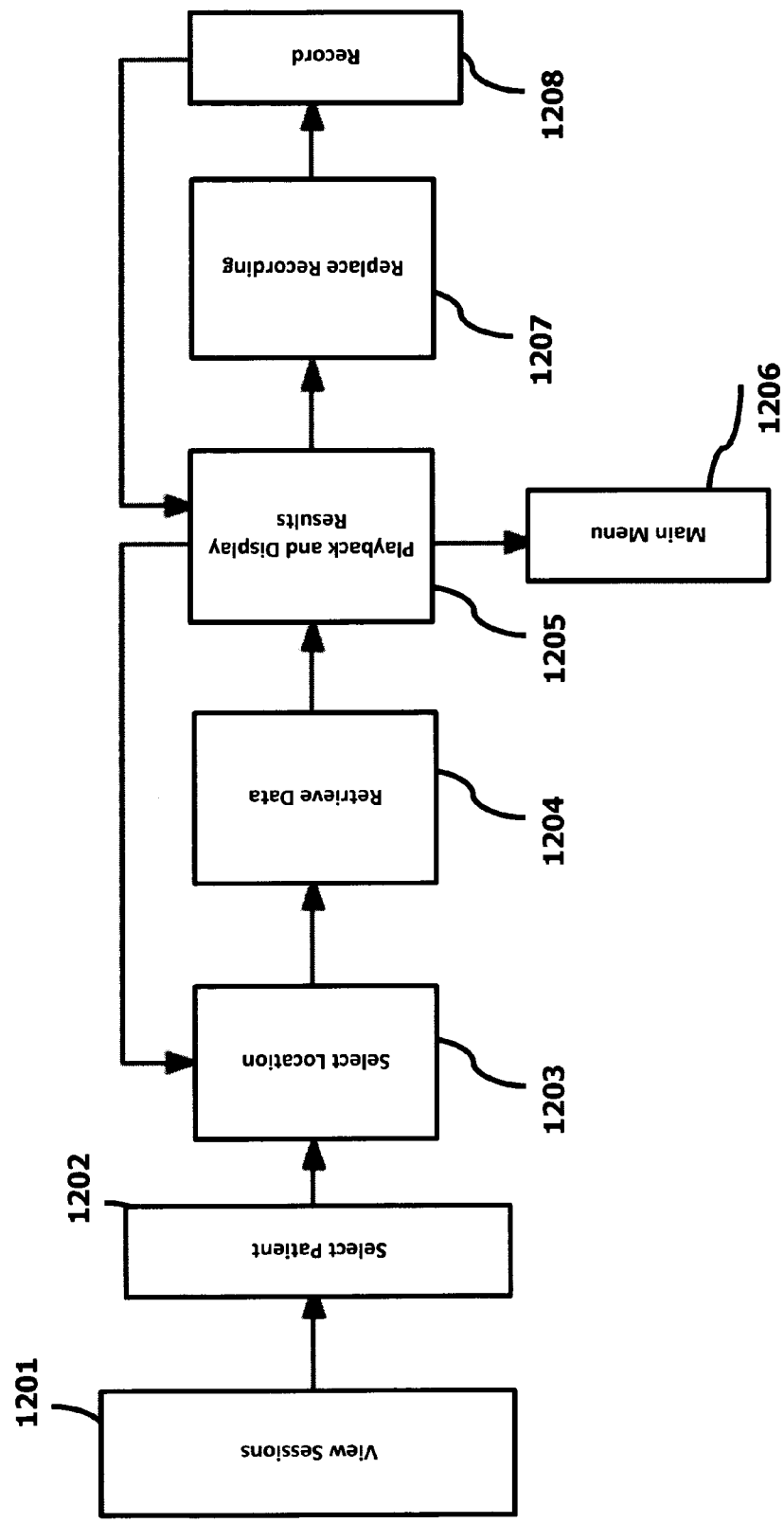
FIG. 12 illustrates viewing of recorded results

Referring to FIG. 12, the user selects view a recording session 1201 by selecting a patient 1202, selects a location 1203 and retrieve the data or recorded results 1204. Results are output on headphones or speakers with sound quality Playback 1205 controls such as Start, Stop, Pause and Volume. For ECGs, distance measurements between two points in milliseconds can be calculated such as Q-T intervals, using on-screen caliper tools. At this point, user can go back to the main menu or 1206 or re-record 1208 or replace the recording 1207.

Figure 16:
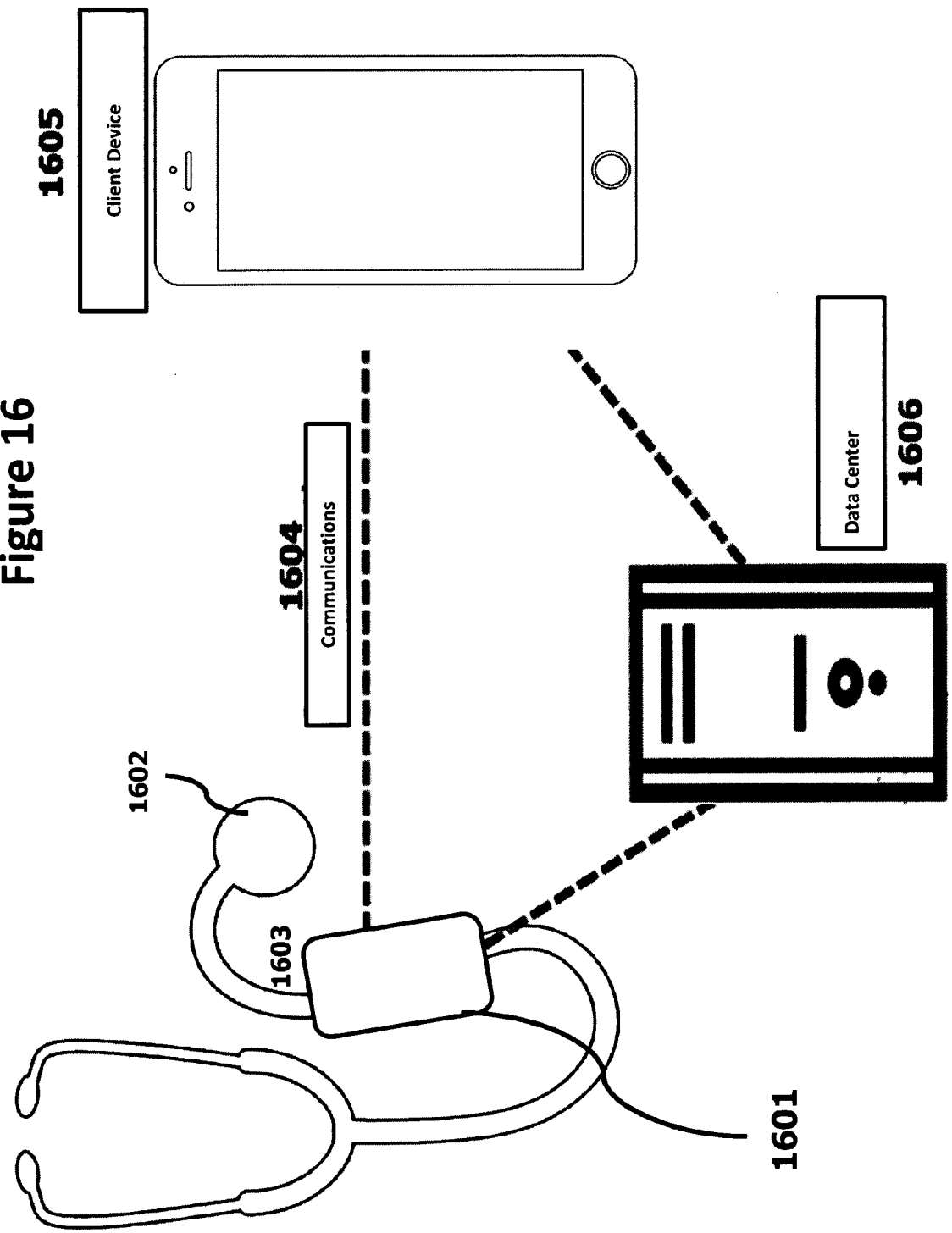
FIG. 16 illustrates the alternative ring Sleeve with alternative enclosure box

In yet another embodiment, FIG. 16 refers to the sensor sleeve 1602, attached to a processing module (referred to as enclosure box (EB)) 1601. The EB contains electronics circuitry that comprises a processor and the corresponding circuitries for biosensor parameters similar to FIG. 5. The Sleeve 1202 is attached to the EB 1601 via an electrical connector 1603. The connector can be standard or micro Universal Serial Bus (USB). The standard USB can be a 2.0 Standard-A type of USB plug, a flattened rectangle which inserts into a "downstream-port" receptacle on the USB host that carries both power and data.

Figure 17:
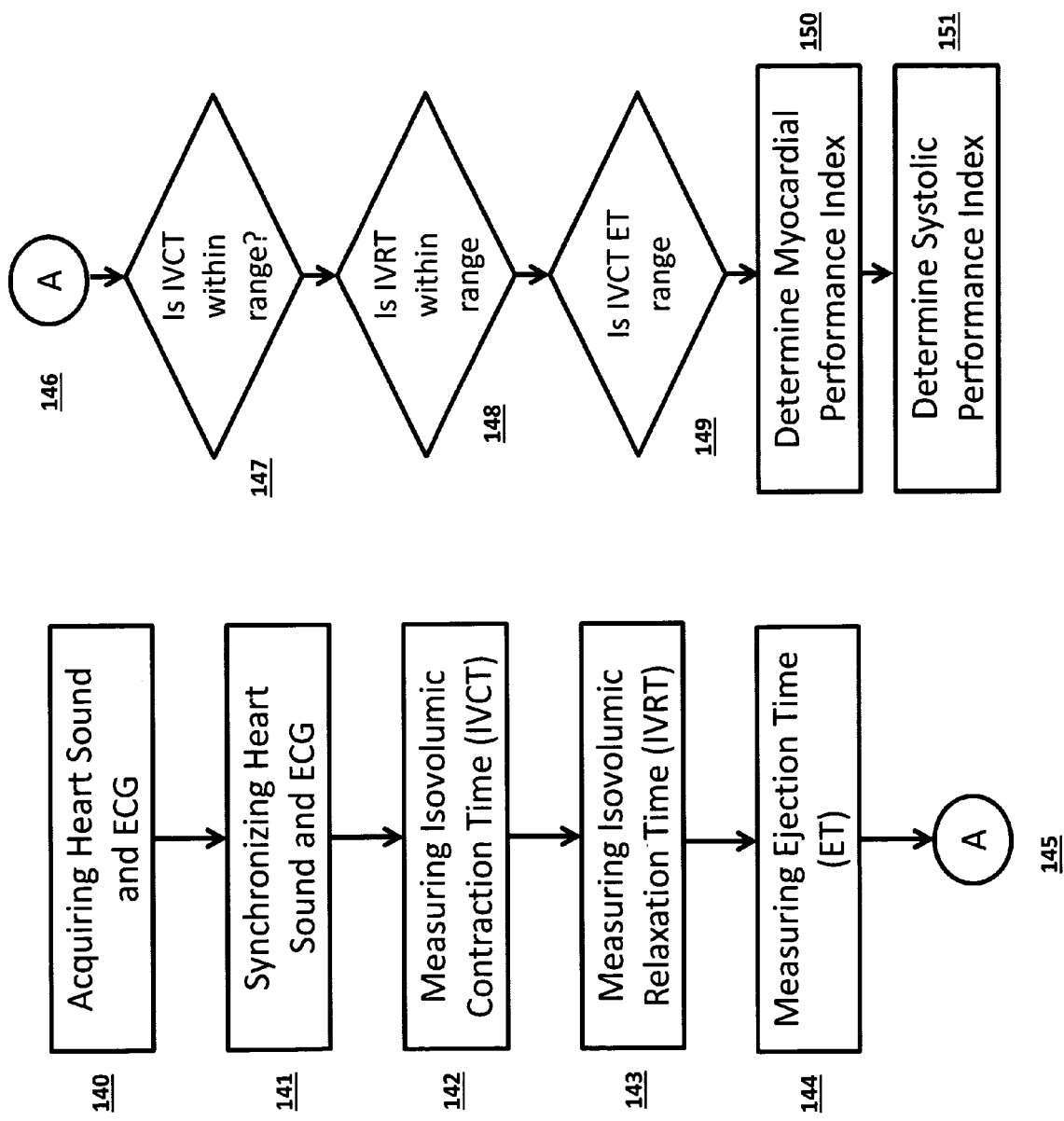
FIG. 17 shows an algorithm of acquiring systolic performance index.

FIG. 17 shows the steps for measuring systolic performance index. Myocardial performance index (MPI) (Tei index) has been regarded as an important parameter in the evaluation of ventricular systolic function in congestive heart failure. MPI is defined as the sum of isovolumic relaxation time (IVRT) and isovolumic contraction time (IVCT) divided by left ventricular ejection time (LVET) ([IVRT+IVCT]/LVET). Systolic performance index (SPI) is the isovolumic or isovolumetric contraction time (the time period between the R peak of the ECG and the first heart sound—S1) divided by ejection period (the time period between the first and second heart sound, S1-S2). Heart sound and ECG are acquired 140 and synchronized 141 by the front-end recorder device (FIG. 1, 100). From there, an algorithm running either on the recorder device (FIG. 1, 100), or the mobile device (FIG. 19, 131 OR FIG. 1, 106) or server device (FIG. 1, 113 OR FIG. 19, item 134) measures the isovolumic contraction 142, shown in FIG. 18 item 150.

Isovolumetric contraction occurs in early systole, during which the ventricles contract with no corresponding volume change, while contraction causes ventricular pressures to rise sharply. The isovolumetric contraction lasts on average about 0.03 s, but this short period of time is enough to build up a sufficiently high pressure that eventually overcomes that of the aorta and the pulmonary trunk upon opening of the semilunar valves, therefore allowing the correct unidirectional flow of blood. The ejection period is also measured 144, which is time period between the first and second heart sound (S1 and S2) FIG. 18, item 151. Isovolumic relaxation time (IVRT) is measure as well 143, an interval in the cardiac cycle, from the aortic component of the second heart sound, that is, closure of the aortic valve, to onset of filling by opening of the mitral valve FIG. 18 item 152 (the time between S2 and the outset of the T wave). A determination is made as to whether or not those parameters are within range (147-149), after which myocardial 150 and systolic performance 151 indices are determined. MPI is measured when the system detects that the user is in sedentary position.

The ejection fraction (EF) is an important measurement in determining how well your heart is pumping out blood and in diagnosing and tracking heart failure. A significant proportion of patients with heart failure happen to have a normal ventricular ejection fraction at echocardiography during examination. Previously called diastolic heart failure, it is nowadays referred to as heart failure with normal ejection fraction (HFNEF) or HF with preserved ejection fraction. EF measures how much blood the left ventricle pumps out with each contraction. A normal heart's ejection fraction may be between 55 and 70%. An ejection fraction of 60% means that 60% of the total amount of blood in the left ventricle is pushed out with each heartbeat.

Systolic performance index (SPI) was found to have a significant inverse correlation with the value of Left Ventricular Ejection Fraction (LVEF ($r=-0.947$; $P<0.001$)), and a significant positive correlation could be seen with the value of Myocardial Performance Index (MPI ($r=0.796$; $P<0.001$)). The sensitivity and specificity of SPI value 0.66 for predicting an LVEF value 55% were found to be 100% and 90.9%, respectively, but the positive and inverse predictive values were 91.3% and 100%, respectively (Yilmaz et al. 2007). SPI is measured when the system detects that the user is in a sedentary position.

Other parameters such as third and fourth heart sounds, and the time that it takes the left ventricular to gather enough to close the mitral valve can be obtained (time period between the start of the QRS complex of the ECG to the first heart sound (S1), when the system detects that the user is in sedentary position.

Figure 18:
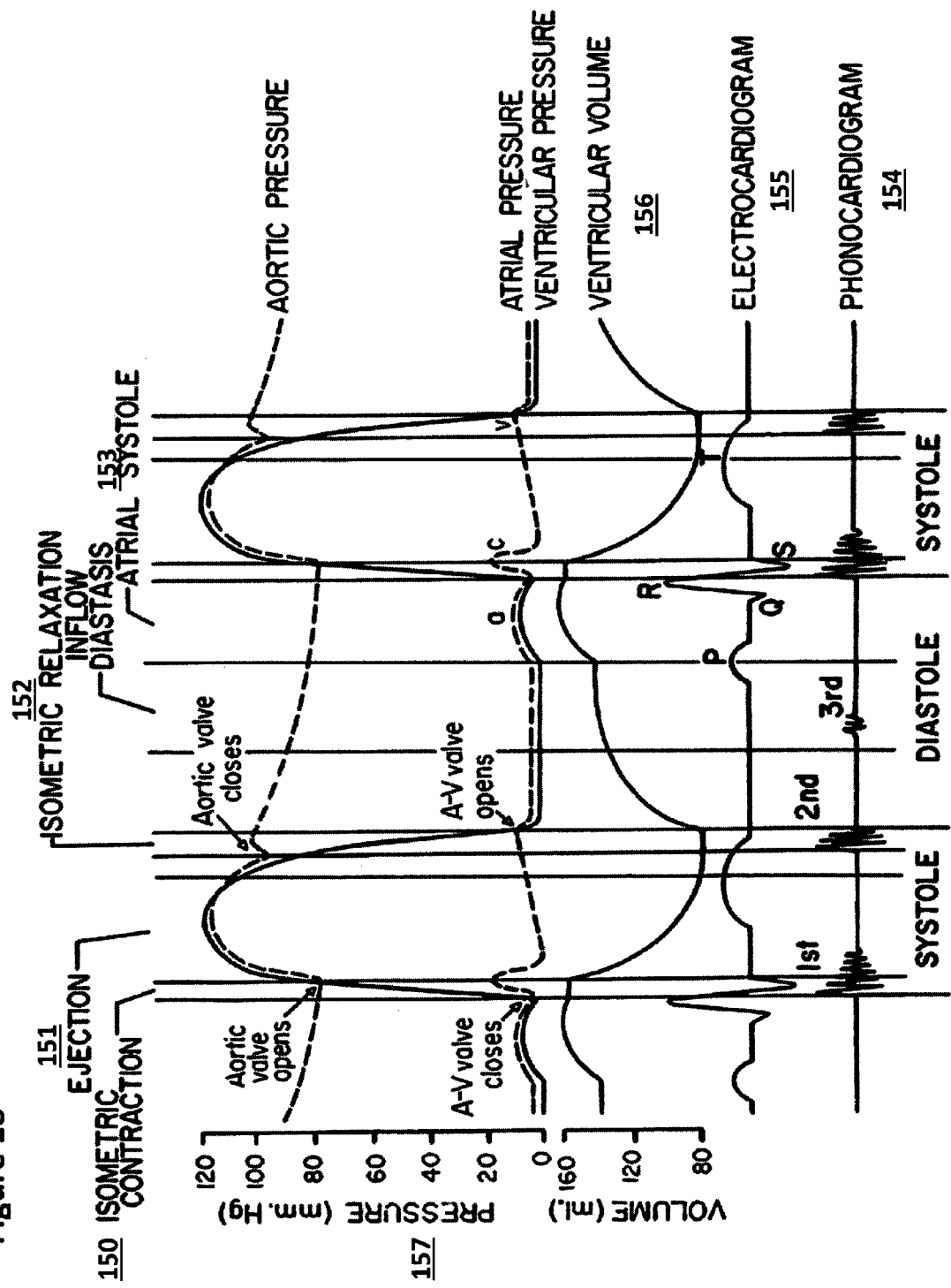
FIG. 18 shows a depiction of the cardiac cycle.

The cardiac cycle FIG. 18 is a period from the beginning of one heart beat to the beginning of the next one. It shows the relationship between the heart's mechanical (phonocardiogram or heart sounds) 154, electrical (ECG) 155, volume 156 and pressure parameters. It consists of two parts:
1. Ventricular contraction called systole.
2. Ventricular relaxation called diastole.

Each part of the cardiac cycle consists of several phases characterized by either a strong pressure change with constant volume or a volume change with a relatively small change in pressure.

Systole includes:
1. Isovolumic contraction time (IVCT) 150.
2. Ejection Time (ET) 151.

Diastole includes:
3. Isovolumic relaxation time (IVRT 152.
4. Rapid ventricular filling.
5. Slow ventricular filling (diastasis).
6. Atrial contraction 153.

The duration of the cardiac cycle is inversely proportional to the heart rate. The cardiac cycle duration increases with a decrease in the heart rate and on the other it shortens with increasing heart rate. At a normal heart rate of 75 beats per minute, one cardiac cycle lasts 0.8 second. Under resting conditions, systole occupies ⅓ and diastole ⅔ of the cardiac cycle duration. At an increasing heart rate (e.g. during an intensive muscle work), the duration of diastole decreases much more than the duration of systole 154.

Arrhythmia Detection: To identify the ST-segment in an ECG signal, accurate detection of the isoelectric line, the J point and the heart rate are required. The isoelectric line is the baseline of the electrocardiogram, typically measured between the T wave offset and the preceding P wave onset. It indicates no muscular activity in the heart at a particular point of time. This is used as a reference to measure ST-segment deviation. The J point is the inflection point at which the QRS complex changes its direction of propagation. It occurs after the offset of the QRS point within a window of 20-50 samples at the rate of 250 Hz of sampling. Our recognition algorithm involves applying three major functions; Discrete Wavelet Transformation (DWT), Windowing Technique, and Slope Detection; on each ECG cycle 155.

With regard to arrhythmia (cardiac rhythm abnormalities) detection, the system is implemented by the Support Vector Machine (SVM) approach. It is a supervised learning framework which performs classification by constructing an N dimensional hyper-plane that optimally separates the data into two categories (S. R. Gunn, "Support Vector Machines for Classification and Regression," Technical Report, Dept. of Electronics and Computer Science, University of Southampton, 1998). It is one of the best learning algorithms that gives the flexibility for the choice of the kernel and performs training in less time when compared to other learning algorithms like neural networks. Every heart beat is represented as a row in the data set with its feature values and its class label. SVM aims to find the optimal separating plane and the data points that determine the position and the orientation of the plane are called the support vectors.

The system was designed to classify six major arrhythmia most commonly observed by the cardiologists. The classes include Normal (N), Premature Ventricular Contraction (V), Premature Atrial Contraction (A), Fusion (F), Right Bundle Branch Block (R), and Left Bundle Branch Block (L). We use two types of features to describe each heart beat or one cardiac cycle, i.e. Morphological Features, an DWT Features.

The system uses 12 morphological features, which give the timing, area, energy and correlation information of the signal. The system uses the ST-segment features such as the slope of the ST segment, the ST-deviation measurement and the correlation coefficients of the signal with templates of each class. Each class is represented by a template manually chosen from the MIT-BIH database (MIT-BIH Arrhythmia Database. www.physionet.org/physiobank/) The correlation coefficient lies between 0 and 1; the higher the coefficient is, the more likely it is for the signal to belong to that class.

Twelve morphological features are being used. They are: (i) QS Width, (ii) Pre RR Interval, (iii) Post RR Interval, (iv) QR Width, (v) RS Width, (vi) Mean Power Spectral Density, (vii) Area Under QR, (viii) Area Under RS, (ix) Autocorrelation Value, (x) ST-segment Deviation, (xi) Slope of ST, (xii) Correlation coefficient with class template. The system uses 191 DWT (Discrete Wavelet Transform) coefficients, which are obtained by a 4 level decomposition of the signal with the db2 mother wavelet. These coefficients are based on the 180 samples taken to represent each heartbeat. Six classifiers are trained, each for identifying one arrhythmia type and using all the heart beats in the databank for training and testing. The six single beat classifiers are: Normal (N) vs. All, Ventricular Contraction (V) vs. All, Premature Atrial Contraction (A) vs. All, Left Bundle Branch Block (L) vs. All, Right Bundle Branch Block (R) vs. All and Fusion (F) vs. All.

Each data sample (heart beat) is represented by its class label and all 191+12=203 feature values, including the morphological and DWT features. Since we perform five-fold cross validation experiments, we use four folds of the data for training the classification system. In particular, we train six classifiers, one for identifying a particular type of beat using the one-versus-all scheme, resulting in six binary beat classifiers. After training, the test data set from the remaining fold (i.e., the fold not used for training) is given to the classification system.

The classification is a two stage process. During the first stage, the training data is generated with the features selected. We have divided the ECG beats into five sets of equal number of beats. One out of the five sets is randomly selected and labeled as Test Data Set. The remaining four sets are labeled as Training Data Sets and are passed into the feature extraction module where each beat is represented with the 203 features. The sets thus obtained are used to train the learning algorithm, SVM, which results in a SVM model file containing all the beats which form the hyper plane for classification. In the second stage, the SVM model file and the Test Data Set are given as the input to the SVM classifier tuned to the selected parameters. The output of the classifier gives the prediction of the class for each beat in the Test Data Set.

Figure 19:
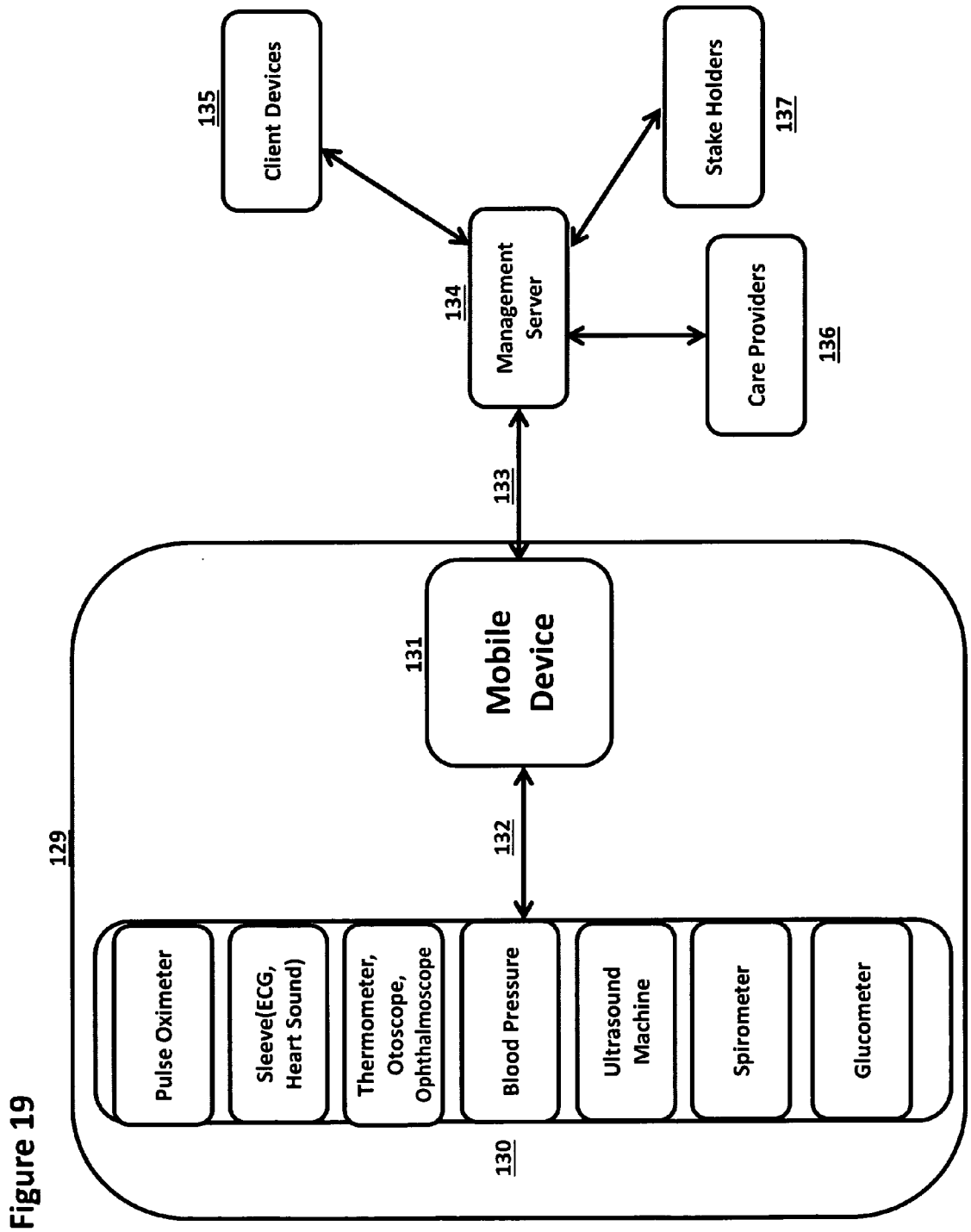
FIG. 19 shows a wall mounted integrated point of care diagnostic system.

In another embodiment, the front-end stethoscope recorder device (FIG. 1, 100) is mounted on the wall, as part of an integrated point-of-care diagnostic system (IPCDS), FIG. 19, 129. The IPCDS 129 consists of diagnostic devices 130 which include the stethoscope recorder device (FIG. 1, 100), a blood pressure monitor, a spirometer, a pulse oximetry, a thermometer, a handheld ultrasound machine, a blood glucose meter, an otoscope and an ophthalmoscope. The diagnostic devices 130 collect data from a user or patient. The data collected includes blood oxygen saturation (SpO2%), heart rate, core body temperature, systolic and diagnostic blood pressure, ECG, heart sound, ultra sound imaging heart murmur and heart failure indication. The data from the diagnostic devices is then transferred to a mobile device 131, such as smartphones and tablets (also FIG. 1, 106) running mobile operating systems such as iOS (Apple) or Android (Google) or Windows (Microsoft), for display and initial analysis via wireless communication, such as infrared communication, Bluetooth and Zigbee or with a wired connection such as USB (Universal Serial Bus) 132. The mobile device 131 can be one of an electronic book, laptop or handheld computer, cellular phone, personal digital assistant (PDA), telehealth gateway or hub and wearable computers. The data is ultimately transferred to a health management server 134 (also FIG. 1, 113) via the Internet, cellular or a private network 133. Other patient medical devices can also collect and transfer the data to the health management server 134 (also FIG. 1, 113). These other patient medical devices include a. pacemaker, a holter monitor, a blood alcohol monitor, an alcohol Breathalyzer, an alcohol ignition interlock, a respiration monitor, an accelerometer, a skin galvanometer, a thermometer, a patient geo-location device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device.

The management server FIG. 19, 134 (also FIG. 1, 113) includes processor(s) and memory storing instructions (software programs) being executed the processor(s) to analyze and score data collected from the diagnostic devices and the other medical devices. The analysis includes the detection of heart murmur, arrhythmia and hear failure. The software programs analyze data received from the diagnostic devices and send notification of data trends that fall below a pre-established threshold to client devices 135 (also FIG. 16, 1605), care providers 136 and to other stake holder client devices 137 such loved ones and family members via the Internet, cellular or a private network. In an alternative embodiment, the IPCDS can be mounted on a mobile cart.

The IPCDS FIG. 19, 129 includes an electrical plug (not shown) and five electrical outlets mounted on the IPCDS. The electrical plug connects to a conventional wall outlet for supplying electrical power to the mobile device 131 and the diagnostic medical devices 130. In another embodiment, the IPCDS includes a power supply for supplying power to the diagnostic medical devices. A structure supports the power supply (e.g., battery or electrical generator), which may be mounted on the IPCDS.

What is claimed is:

1. A method of determining and using a mechanical and electrical footprint of the heart comprising:
   a. Configuring a stethoscope front-end recorder sleeve device with biological sensors to acquire an electrical footprint of the heart;
   b. Configuring the stethoscope front-end recorder sleeve device to acquire a mechanical footprint of the heart;
   c. Synchronizing the mechanical and electrical footprints of the heart;
   d. Determining via a processor normal and pathological heart sounds from the mechanical footprint of the heart, and normal and abnormal heart rhythms from the electrical footprint of the heart;
   e. Determining via the processor a time period between an R peak of the electrical footprint of the heart and a first heart sound of the mechanical footprint;
   f. Determining via the processor a time period between the first heart sound and a second heart sound of the mechanical footprint of the heart;
   g. Calculating a systolic performance index (SPI) from the time period between the R peak of the electrical footprint of the heart and the first heart sound, and the time period between the first and second heart sounds of the mechanical footprint of the heart;
   h. Correlating a left ventricular ejection fraction parameter from the SPI calculation.

2. The method according to claim 1, further comprising of determining the time period between aortic component of a second heart sound to onset of filling by opening of a mitral valve.

3. The method according to claim 1 wherein the heart's electrical and mechanical footprints are transmitted to a mobile device.

4. The method according to claim 1 wherein electrical footprint of the heart is electrocardiogram (ECG).

5. The method according to claim 1 wherein mechanical footprint further includes the acquisition of blood oxygen saturation.

6. A system for determining and using a mechanical and electrical footprint of the heart comprising:
   A stethoscope front-end sleeve recorder device that contains a processor, biological sensors, and a memory for storing instructions being executed by the processor to perform the following:
   a. Acquiring an electrical footprint of the heart;
   b. Acquiring a mechanical footprint of the heart;
   c. Synchronizing the mechanical and electrical footprints of the heart;
   d. Determining normal and pathological heart sounds from the mechanical footprint of the heart, and normal and abnormal heart rhythms from the electrical footprint of the heart;
   e. Determining a time period between a R peak of the electrical footprint of the heart and a first heart sound of the mechanical footprint;
   f. Determining a time period between the first and a second heart sound of the mechanical footprint;
   g. Calculating a systolic performance index (SPI) from the time period between a R peak of the electrical footprint of the heart and the first heart sound, and the time period between the first and second heart sounds of the mechanical footprint of the heart;
   h. Correlating a left ventricular ejection fraction parameter from the SPI calculation.

7. The system according to claim 6, further comprising determining a time period between an aortic component of the second heart sound to an onset of filling by opening of a mitral valve.

8. The system according to claim 6, wherein a myocardial performance index is derived.

9. The system according to claim 6 wherein the heart's electrical and mechanical footprints are transmitted to a mobile device.

* * * * *